United States Patent
Forsell

(10) Patent No.: US 8,862,241 B2
(45) Date of Patent: Oct. 14, 2014

(54) SYSTEM FOR SUPPLYING ENERGY TO AN IMPLANTABLE MEDICAL DEVICE

(76) Inventor: Peter Forsell, Bouveret (CH)

( * ) Notice: Subject to any disclaimer, the term of this patent is extended or adjusted under 35 U.S.C. 154(b) by 153 days.

(21) Appl. No.: 13/130,634

(22) PCT Filed: Nov. 23, 2009

(86) PCT No.: PCT/SE2009/000501
§ 371 (c)(1),
(2), (4) Date: Aug. 3, 2011

(87) PCT Pub. No.: WO2010/059097
PCT Pub. Date: May 27, 2010

(65) Prior Publication Data
US 2011/0301668 A1    Dec. 8, 2011

Related U.S. Application Data

(60) Provisional application No. 61/193,368, filed on Nov. 21, 2008, provisional application No. 61/213,225, filed on May 19, 2009, provisional application No. 61/213,805, filed on Jul. 17, 2009.

(30) Foreign Application Priority Data

May 11, 2009   (SE) ........................................ 0900636
Jul. 17, 2009   (SE) ........................................ 0901002

(51) Int. Cl.
A61N 1/08    (2006.01)
A61N 1/378   (2006.01)
A61N 1/372   (2006.01)
H01F 38/14   (2006.01)
H02J 7/02    (2006.01)

(52) U.S. Cl.
CPC ........... *A61N 1/3787* (2013.01); *A61N 1/37229* (2013.01); *A61N 1/37223* (2013.01); *H01F 38/14* (2013.01); *H02J 7/025* (2013.01)
USPC ................... 607/60; 607/32; 607/33; 607/61

(58) Field of Classification Search
USPC .......................................... 607/60, 61, 32, 33
See application file for complete search history.

(56) References Cited

U.S. PATENT DOCUMENTS 4,696,287 A * 9/1987 Hortmann et al. .............. 607/57
5,314,453 A   5/1994 Jeutter
(Continued)

FOREIGN PATENT DOCUMENTS

EP    1 513 241    3/2005
WO    WO 99/42176  8/1999
(Continued)

OTHER PUBLICATIONS

International Search Report for PCT/SE2009/000501, dated Mar. 4, 2010.
(Continued)

*Primary Examiner* — Niketa Patel
*Assistant Examiner* — Christopher A Flory

(57) ABSTRACT

An implanted coil supplies energy or control signals to, or provides information from, a medical device implanted in a human or animal patient. Preferably, the coil is implanted subcutaneously in the patient at a location suitable for easy access to the coil. The implanted coil is wound from a wire that is formed into a plurality of smaller diameter coils connected in series and positioned perpendicular to the larger implanted coil. Preferably, the wire used to form the implanted coil is a helically-shaped wire that is very resilient, and, thus, capable of handling even extreme movements of a patient in whom it is implanted without the risk of breaking.

22 Claims, 14 Drawing Sheets

(56) References Cited

U.S. PATENT DOCUMENTS

| | | | |
|---|---|---|---|
| 5,853,418 A | 12/1998 | Ken et al. | |
| 6,067,991 A * | 5/2000 | Forsell | 128/899 |
| 6,456,883 B1 | 9/2002 | Torgerson et al. | |
| 6,542,777 B1 | 4/2003 | Griffith et al. | |
| 6,937,894 B1 | 8/2005 | Isaac et al. | |
| 2003/0032857 A1* | 2/2003 | Forsell | 600/30 |
| 2003/0060857 A1 | 3/2003 | Perrson et al. | |
| 2003/0078634 A1* | 4/2003 | Schulman et al. | 607/61 |
| 2003/0109771 A1* | 6/2003 | Forsell | 600/38 |
| 2003/0144575 A1* | 7/2003 | Forsell | 600/29 |
| 2005/0065501 A1 | 3/2005 | Wallace | |
| 2005/0107847 A1 | 5/2005 | Gruber et al. | |
| 2005/0154426 A1 | 7/2005 | Boveja et al. | |
| 2005/0165461 A1* | 7/2005 | Takeda et al. | 607/61 |
| 2006/0085041 A1* | 4/2006 | Hastings et al. | 607/33 |
| 2006/0206170 A1 | 9/2006 | Denker et al. | |
| 2007/0112344 A1* | 5/2007 | Keilman | 606/41 |
| 2007/0191816 A1 | 8/2007 | Behan et al. | |
| 2007/0219590 A1* | 9/2007 | Hastings et al. | 607/9 |
| 2007/0287969 A1 | 12/2007 | Rezai et al. | |
| 2008/0046040 A1 | 2/2008 | Denker et al. | |
| 2009/0005859 A1* | 1/2009 | Keilman | 623/1.42 |

FOREIGN PATENT DOCUMENTS

| | | |
|---|---|---|
| WO | WO 01/37926 | 5/2001 |
| WO | WO 03/039652 | 5/2003 |
| WO | WO 2009/051539 | 4/2009 |
| WO | WO 2011/008163 | 1/2011 |

OTHER PUBLICATIONS

Written Opinion for PCT/SE2009/000501, dated Mar. 4, 2010.
Extended European Search Report for European Patent Application No. 09827812.0 dated Sep. 17, 2012.

* cited by examiner

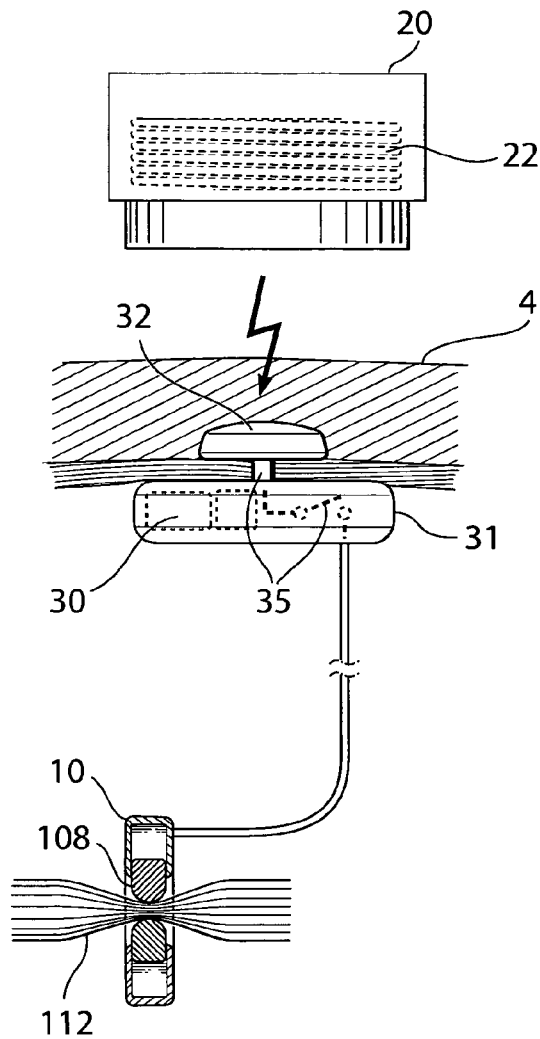
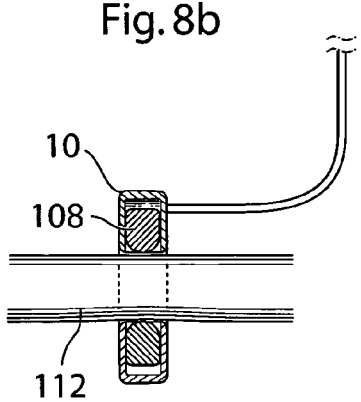
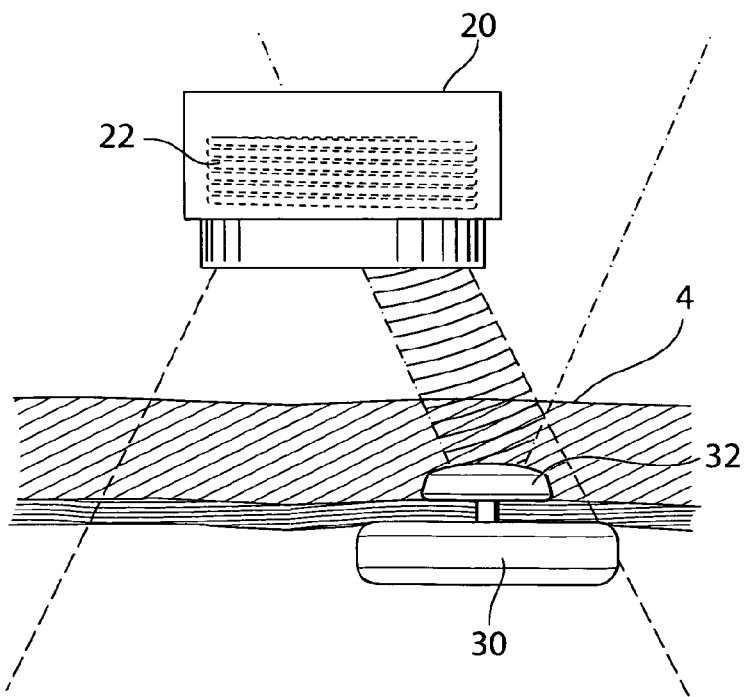

SYSTEM FOR SUPPLYING ENERGY TO AN IMPLANTABLE MEDICAL DEVICE

This application is the U.S. national phase of International Application No. PCT/SE2009/000501 filed 23 Nov. 2009 which designated the U.S. and claims benefit of U.S. 61/193,368 filed 21 Nov. 2008, 61/213,225 filed 19 May 2009 and U.S. 61/213,805 filed 17 Jul. 2009 and claims priority to SE 0900636-2 filed 11 May 2009 and SE 0901002-6 filed 17 Jul. 2009, the entire contents of each of which are hereby incorporated by reference.

The present invention relates to medical implants, and, more particularly, to an improved coil for supplying energy or control signals to, or information from, a medical device implanted in a human or animal patient's body.

BACKGROUND OF THE INVENTION

Medical devices are implanted in humans or animals for many reasons. Some of these devices are used to monitor one or more bodily functions. Other devices are used to stimulate or out rightly control bodily functions. Often, the medical devices will include some kind of communications circuit for receiving signals used to power and/or control the devices, or for sending outside a patient's body information about the medical device or bodily functions monitored or controlled by the device. Typically, medical devices are powered by an electric power supply, such as a battery, that provides the voltage and current needed for their operation.

Medical devices are often intended to be implanted in a patient's body for many years, and in some instances, for the rest of a patient's life. As such, the power supplies used to power these long-term medical devices are implanted in a patient at a location that permits easy access from outside the patient's body for recharging or replacement of the power supply. Typically, these power supplies are recharged by energy drawn from an alternating magnetic field transmitted from outside of a patient's body to inside of the patient's body using a pair of coils. The pair of coils includes a first coil that is part of a transmitter that generates the alternating magnetic field and a second coil that is part of a receiver that is also implanted in a patient's body. Alternatively, the second coil implanted in a patient's body may be connected directly to a power supply or a medical device implanted in the patient. Because the second coil is often implanted subcutaneously in a patient to permit easy access to it from outside of the patient's body, there is a risk that the second coil, over time, may become intermittently inoperable, or even completely fail, because movements of the patient over time cause the secondary coil to break. Thus, it would be desirable to provide a coil that can be implanted in a patient at a location that is easily accessible and that would reliably operate over time, notwithstanding bending of the coil caused by a patient's movements over time.

BRIEF DESCRIPTION OF THE INVENTION

The present invention is directed to an improved coil for supplying energy or control signals to, or providing information from, a medical device implanted in a human or animal patient where the medical device is used to monitor one or more bodily functions or to stimulate or out rightly control one or more bodily functions.

Preferably, the coil is implanted in a patient at a location that permits easy access to the coil from outside of the patient's body. Preferably, the coil is implanted subcutaneously in a patient at a suitable location for such easy access.

Where the coil is implanted in a patient to supply energy to an energy-consuming implanted medical device, the coil can be connected to an implanted control device which, in turn, is connected to an implanted power supply connected to an implanted medical device, or directly to the implanted medical device. Alternatively, the coil can be connected to the implanted power supply connected to the medical device, or directly to the implanted medical device.

Where the coil is implanted in a patient to receive control signals for controlling the operation of an implanted medical device, the implanted coil is preferably connected to an implanted control device that is a receiver which, in turn, is connected to the implanted medical device. Where the implanted coil also transmits information from the implanted medical device, the coil is preferably connected to an implanted control device that is a transceiver which, in turn, is connected to the implanted medical device. The transceiver functions to receive control signals received by the coil and to provide informational signals to the coil for transmission outside of the patient's body.

The implanted coil, which performs the foregoing communications functions, is wound from a wire that is formed into a plurality of smaller diameter coils connected in series. As this wire is wound to form the implanted coil, the smaller diameter coils are caused to be positioned perpendicular to the longitudinal axis of the larger implanted coil. Preferably, the wire used to form the implanted coil is a helically-shaped wire that is very resilient, and, thus, capable of handling, without the risk of breaking, even extreme movements of a patient in whom it is implanted.

In one embodiment, the first coil comprises one single winding.

In one embodiment, the first coil comprises a plurality of windings.

In one embodiment, the first coil is substantially larger than the second coil.

In one embodiment, the first coil is implanted in the stomach area of the patient.

In one embodiment, the first coil is implanted in the back area of the patient.

In one embodiment, the first coil is adapted to have an irregular cross-sectional shape.

The inventive system is arranged to determine a balance between the amount of energy received in the energy receiver and the amount of energy used by the medical device, and the internal control unit is arranged to wirelessly transmit feedback information to the external control unit.

According to the invention, the system is arranged to determine the feedback information based on or relating to a first and a second parameter. The first parameter is based on the previously mentioned energy balance seen over a certain amount of time, and the second parameter is based on information determined by the system and relating to a coupling factor between the primary and the secondary coil.

The system of the invention is adapted to take into account at least both the first and second parameters in order to determine the amount of energy which should be transmitted by the external energy source, thus allowing for a rapid adjustment of said energy balance.

In one embodiment of the system of the invention, the system also comprises a capacitor connected in parallel over the medical device, and the system is arranged to determine the total amount of energy stored in the capacitor. In this embodiment, the feedback information is also based on or comprises a third parameter which comprises or is based on the total amount of energy stored in the capacitor. The system is also, in this embodiment, adapted to take into account the third parameter in order to determine the amount of energy which should be transmitted by the external energy source.

In one embodiment of the system of the invention, the medical device also comprises a current regulator arranged to keep a current constant, and the system is arranged to determine a difference between an input current to the current regulator and the current which the current regulator is arranged to keep constant. In such a system, the feedback information is also based on or comprises a third parameter which comprises or is based on the current difference, and the system is adapted to also take into account the third parameter in order to determine the amount of energy which should transmitted by the external energy source.

In one embodiment of the system of the invention, the medical device also comprises a voltage regulator arranged to keep a voltage constant and the system is arranged to determine a difference between an input voltage to the voltage regulator and the voltage which the voltage regulator is arranged to keep constant. In such a system, the feedback information is also based on or comprises a third parameter which comprises or is based on the voltage difference, and the system is adapted to also take into account this third parameter in order to determine the amount of energy which should transmitted by the external energy source.

In one embodiment, the system is adapted to use all three parameters to determine the feedback information, and the feedback information comprises information comprising or relating to the amount of energy which should be transmitted by the external energy source.

In one embodiment, the system is adapted to use the second and third parameters for determining the amount of energy which should be transmitted by the external energy source, and to use the first parameter during operation of the system in order to determine the amount of energy which should be transmitted by the external energy source during operation of the system.

Suitably, the external control unit is adapted to transmit information wirelessly to the internal control unit which in turn is adapted to receive information wirelessly.

As will be realized, when it comes to determining the feedback parameters, this task can be divided between the internal and the external units (suitably their respective control units) in a rather large number of ways within the scope of the invention. In one embodiment, the external control unit can supply the internal control unit with information necessary to determine the second parameter, and the internal control unit can be given the task of determining all of the parameters as such, and to then supply them to the external control unit as feedback information. In such an embodiment, it is sufficient if the internal control unit supplies the external control unit with a percentage figure for a variation of the energy supply as the feedback information. Naturally, the percentage can be positive, negative or zero, in order to indicate an increase, a decrease, or a maintained energy transfer level.

In another embodiment, the internal control unit supplies the external control unit with information which is sufficient for the external control unit to establish the parameters which are used by the system, with that information then being the feedback information.

Again, as will be realized, the task of determining the feedback parameters can be divided in a large number of ways between the internal and external units within the scope of the invention, which will also impact on the nature and contents of the feedback information.

Thus, in one embodiment, at least one of the parameters is transmitted from the external control unit to the internal control unit, and the internal control unit determines the other parameters used by the system and transmits the feedback information to the external control unit as information on the amount of energy which should transmitted by the external energy source.

In one embodiment, information for determining at least one of the parameters is transmitted from the external control unit to the internal control unit, and the internal control unit determines the parameters used by the system and transmits the feedback information to the external control unit as information on the amount of energy which should transmitted by the external energy source.

In one embodiment, information for determining at least one of the parameters is transmitted as the feedback information from the internal control unit to the external control unit, and the external control unit determines the parameters used by the system as well as the amount of energy which should transmitted by the external energy source.

In one embodiment, at least one of the parameters is transmitted as the feedback information from the internal control unit to the external control unit, and the external control unit determines the other parameters used by the system as well as the amount of energy which should transmitted by the external energy source. In an embodiment a system for supplying energy to an implanted medical device or to a medical device suited for implantation in a patient's body is provided. The system can comprise an internal power supply that is arranged to be implanted in the patient's body and is associated with, such as including or connected to, a first coil. The system can further comprise an external power supply comprising a second coil arranged to charge the internal power supply by wireless transmission of energy to the internal power supply. The system may further comprise a wireless feedback system arranged to actively transmit feedback information that is related to the amount of energy that is received in a receiver associated with, such as included in or connected to, the internal power supply, the feedback information being transmitted out of the body. The feedback information can e.g. be related to the coupling factor between the first coil and the second coil. Thereby, an optimal position of the external power supply, in particular of the coil thereof, for charging the internal power supply can be found, which in turn results in a better charging of the internal power supply.

In an embodiment the system can comprise a unit for analyzing the feedback information, such as for comparing the amount of received energy to the amount of energy transmitted by the external power supply.

In an embodiment the external power supply can be arranged to be moved in relation to the internal power supply, and then it may comprise a unit for detecting an increase of the coupling factor.

In an embodiment the external power supply can be arranged to increase the amount of energy transmitted to the internal power supply until a response is detected by the external power supply, the response including feedback information relating to the value of the coupling factor.

A use of the methods, devices and systems as described herein may, at least in some cases, provide an efficient transfer of energy, and in many cases also a more efficient transfer of energy, than in existing systems, from an external power supply, also called external charger, to an internal power supply arranged to supply power to an implanted medical device.

Any feature in any of the four combinations of features in the combination embodiments described below may be used in any combination and furthermore in combination with any other feature or embodiment described or disclosed in any of the drawings, text and description of the present this application.

First combination embodiments including electrical switching technology

A system supplying energy to an implantable medical device when implanted in a patient's body, comprising an internal power supply arranged to be implanted in the patient's body for supplying energy to said implanted medical device, comprising a receiver comprising a first coil, an external power supply arranged to charge said internal power supply, wirelessly transmitting energy to supply the internal power supply with energy, the external power supply comprising a second coil, and a power switch to switch said first coil on and off from connection with said medical device, and a control unit arranged to control a transmission of feedback information related to the charging received in said internal power supply, received as an impedance variation in the second coil load, when said switch switches said first coil on and off.

A system, wherein the external power supply is arranged to be moved in relation to the internal power supply, resulting in an impedance variation depending on the position of said external power supply.

A system, wherein the external power supply is arranged to detect a maximum impedance variation when moved in relation to the internal power supply.

A system, further comprising an indicator arranged to indicate a better energy supply to the internal power supply in response to an increased impedance variation.

A system, wherein the external power supply is adapted to calibrate the system by increasing the amount of transferred energy to the internal power supply until a response of said impedance variation is detected.

A system, wherein the external power supply further comprises an indicator arranged to indicate a change in said impedance variation.

A system, wherein the external power supply comprises an analyzer arranged to analyze the impedance variations detected and arranged to indicate an optimal placement of said second coil in relation to said first coil based on the analyzed impedance variations.

A system, wherein the external power supply comprises a display arranged to display and/or indicate the feedback information or information derived therefrom.

A system, wherein the display comprises a number of differently colored light sources.

An internal power supply arranged to be implanted in the patient's body for supplying energy to an implanted medical device, the internal power supply comprising a receiver comprising a first coil arranged to be charged with energy wirelessly transmitted from an external power supply, wherein the internal power supply is associated with a power switch to switch said first coil on and off from connection with said medical device, and further comprising a control unit arranged to control transmission of a feedback information related to the charging received in said internal power supply, received as an impedance variation in the coil load, when said switch switches said first coil on and off.

An external power supply arranged to charge an internal power supply comprising a first coil and arranged to supply an implanted medical device with energy, the external power supply arranged to wirelessly transmit energy to supply the internal power supply with energy, the external power supply comprising a second coil, the external power supply further comprising a receiver for receiving feedback information related to the charging received in said internal power supply as an impedance variation in the first coil load, when the connection between the first coil and the implanted medical device is switched on and off.

An external power supply, wherein the external power supply is arranged to be moved in relation to the internal power supply, resulting in an impedance variation depending on the position of said external power supply.

An external power supply, further comprising an indicator arranged to indicate a better energy supply to the internal power supply in response to an increased impedance variation.

A external power supply, wherein the external power supply is arranged to increase the amount of transferred energy to the internal power supply until a response of said impedance variation is detected.

An external power supply, wherein the external power supply further comprises an indicator arranged to indicate a change in impedance variation.

An external power supply, wherein the external power supply comprises an analyzer arranged to analyze the impedance variations detected and arranged to indicate an optimal placement of said second coil in relation to said first coil based on the analyzed impedance variations.

An external power supply, wherein the external power supply comprises a display arranged to display the feedback information or information derived therefrom.

An external power supply, wherein the display comprises a number of differently colored light sources.

A method for supplying energy to an implanted medical device comprising an internal power supply arranged to be implanted in a patient's body, the internal power supply comprising a receiver comprising a first coil and a power switch, the device further comprising an external power supply comprising a second coil, the method comprising the steps of:

charging said internal power supply using wirelessly transmission of energy to the internal power supply, switching said first coil on and off from connection with said medical device, transmitting feedback information related to the charging received in said internal power supply, and receiving said feedback information as an impedance variation in the second coil load, in response to switching said first coil on and off.

A method, further comprising the step of moving the external power supply in relation to the internal power supply.

A method, further comprising the step of increasing the amount of transferred energy to the internal power supply until a response of said impedance variation is detected.

A method, further comprising the step of indicating a positive or negative change in the impedance variation.

A method, further comprising the step of indicating an optimal placement of said second coil in relation to said first coil in response to a maximal impedance variation.

A method, further comprising the steps of:
analyzing the impedance variation, and
optimizing the placement for maximum impedance variation of said second coil in relation to said first coil based on the analyzed impedance variations.

A method, further comprising the step of generating a signal indicative of the impedance variation.

A method, further comprising the step of indicating and/or displaying the feedback information or information derived therefrom.

A method, wherein the displayed feedback information is displayed by a number of differently colored light sources.

A method of using the features above, comprising the steps of:
creating an opening in the skin of a mammal patient,
dissecting an one area of the patient,
placing the internal power supply device within said area,
charging said internal power supply postoperatively and non-invasively by
wirelessly transmitting energy from an external power supply, said internal power supply further comprising a switch connecting said internal power supply with said medical implant,
switching said switch on and off,
wirelessly receiving feedback information from the internal power supply out of the patient's body as impedance variation, when said switch switching on and off.

A method, comprising the step of moving said external power supply, maximizing said impedance variation, and optimizing the placement of said external power supply in relation to said internal power supply.

A method, wherein the step of creating an opening in the skin comprises:
inserting a tube or needle into the patient's body,
filling the body through the tube or needle with a gas and thereby expanding a cavity within the patient's body,
inserting at least two laparoscopic trocars into said cavity,
inserting at least one camera through at least one laparoscopic trocar,
inserting at least one dissecting tool through at least one laparoscopic trocar.

Second combination embodiments including passive electromagnetic feedback technology A system for supplying energy to an implantable medical device when implanted in a patient's body, comprising
an internal power supply arranged to be implanted in the patient's body, comprising a receiver comprising a first coil,
an external charger arranged to wirelessly transmit energy to charge said internal power supply with energy, the external power supply comprising a second coil, and
a receiver in the external power supply for receiving passively transmitted feedback information from the first coil generated in response to a power pulse or burst transmitted by the external power supply.

A system, wherein the receiver is arranged to determine the strength of said electromagnetic field generated by the first coil.

A system, wherein the external power supply is arranged to be moved in relation to the internal power supply, and wherein the external power supply comprises an indicator arranged to indicate a response to said energy pulse or burst depending on the position of said external power supply.

A system, wherein the external charger is arranged to display the determined strength of said electromagnetic field when the external power supply is moved in relation to said internal power supply.

A system, wherein the external power supply is arranged to increase the amount of transferred energy to the internal power supply until a response of said bursts/pulses is detected.

A system, wherein the external power supply comprises an analyzer arranged to display the strength or magnitude of the detected electromagnetic field.

A system, wherein the external power supply further comprises a sensor arranged to generate a signal indicative of a magnetic field returning from the first coil.

A system, wherein the external power supply comprises a display arranged to display the feedback information or information derived therefrom.

A system, wherein the display comprises a number of differently colored light sources.

A method of supplying energy to an implanted medical device, the device comprising an internal power supply implanted in the patient's body comprising a first coil, the device further comprising an external charger having a second coil, the method comprising the steps of:
wirelessly transmitting energy from the external charger to the internal power supply charging said internal power supply with energy, and
receiving in the external power supply passively transmitted feedback information from the first coil generated in response to a power pulse or burst transmitted by the external power supply.

A method, further comprising the step of determining in the external power supply the strength of said electromagnetic field generated by the first coil.

A method, further comprising the steps of:
moving the external power supply in relation to the internal power supply, and
indicating a response to said energy pulse or burst.

A method, further comprising the step of indicating the position where the response is maximized as optimal position of said external power supply.

A method, further comprising the step of increasing the amount of transferred energy to the internal power supply until a response of said bursts/pulses is detected.

A method, further comprising the step of indicating or displaying the strength or magnitude of the detected electromagnetic field.

A method, further comprising the step of generating a signal indicative of a returning magnetic field from the first coil.

A method, further comprising the step of indicating or displaying the feedback information or information derived therefrom.

A method, wherein the displayed feedback information is displayed by a number of differently colored light sources.

Third combination embodiments including coupling factor technology

A system for supplying energy to an implantable medical device when implanted in a patient's body, the system comprising:
an internal power supply arranged to be implanted in the patient's body, comprising a receiver comprising a first coil,
an external power supply comprising a second coil arranged to charge said internal power supply using wireless transmission of energy to the internal power supply, and
a wireless feedback system arranged to actively transmit feedback information related to the received amount of energy in the receiver, out of the body, wherein the feedback information is related to the electromagnetic coupling such as the coupling factor between the first and second coils.

A system further comprising a unit for comparing the feedback information to the amount of energy transmitted by the external power supply.

A system, wherein the external power supply is arranged to be moved in relation to the internal power supply, and further comprising a unit for detecting an increase or decrease in the electromagnetic coupling such as said coupling factor.

A system, wherein the external power supply is arranged to increase the amount of transferred energy to the internal power supply until a response of said coupling factor is detected.

A system, wherein the external power supply further comprises an indicator arranged to indicate a positive or negative change in the electromagnetic coupling such as the coupling factor.

A system, wherein the external power supply further comprises an indicator arranged to indicate an optimal placement of said second coil in relation to said first coil to optimize the electromagnetic coupling such as said coupling factor.

A system, wherein the external power supply is freely movable to an optimal placement position of said second coil in relation to said first coil.

A system, wherein the external power supply further comprises an analyzer arranged to analyze the amount of energy being transmitted and arranged to receive feedback information related to the amount of energy received in the receiver, and further arranged to determine a value of the electromagnetic coupling such as the coupling factor by comparing the amount of transmitted energy and the feedback information related to the amount of received information.

A system, wherein the external power supply further comprises a sensor arranged to generate a signal indicative of the coupling factor.

A system, wherein the external power supply comprises a display arranged to display the feedback information or information derived therefrom.

A system, wherein the display comprises a number of differently colored light sources.

An internal power supply arranged to be implanted in a patient's body, comprising a receiver comprising a coil, wherein the internal power supply is arranged to be charged via using wireless transmission of energy to the internal power supply, and further comprising a wireless feedback system arranged to actively transmit feedback information related to the received amount of energy in the receiver, out of the body, wherein the feedback information is related to the amount of energy being received.

An external power supply comprising a second coil arranged to charge an implantable power supply comprising a first coil using wireless transmission of energy to the internal power supply, the external power supply further comprising a receiver for receiving actively transmitted feedback information related to the received amount of energy in the implantable power supply, wherein the feedback information is related to the coupling factor between the first and second coils.

An external power supply, wherein the power supply further comprises a unit for comparing the feedback information to the amount of energy transmitted by the external power supply.

An external power supply, wherein the external power supply is arranged to be moved in relation to the internal power supply, and further comprising a unit for detecting an increase in said coupling factor, to allow to maximize said increase.

An external power supply, wherein the external power supply is arranged to increase the amount of transferred energy to the internal power supply until a response of said coupling factor is detected.

An external power supply, wherein the external power supply further comprises an indicator arranged to indicate a positive or negative change in the coupling factor.

An external power supply, wherein the external power supply further comprises an indicator arranged to indicate an optimal placement of said second coil in relation to said first coil to optimize said coupling factor.

An external power supply, wherein the external power supply further comprises an analyzer arranged to analyze the amount of energy being transmitted and arranged to receive feedback information related to the amount of energy received in the receiver, and further arranged to determine the coupling factor by comparing the amount of transmitted energy and the feedback information related to the amount of received energy.

An external power supply, wherein the external power supply further comprises a sensor arranged to generate a signal indicative of the coupling factor.

An external power supply, wherein the external power supply comprises a display arranged to display the feedback information.

An external power supply, wherein the display comprises a number of differently colored light sources.

A method of energy transfer to an implanted medical device in a patient's body, the device comprising an internal power supply comprising a receiver comprising a first coil from an external power supply comprising a second coil, the method comprising the steps of:
charging said internal power supply using wireless transmission of energy to the internal power supply, and
wirelessly transmitting feedback information related to the received amount of energy in the receiver, out of the body, wherein the feedback information is related to the electromagnetic coupling such as the coupling factor between the first and second coils.

A method, wherein the method further comprises the step of comparing the feedback information to the amount of energy transmitted by the external power supply.

A method further comprising the step of:
moving the external power supply in relation to the internal power supply, and
detecting an increase in said coupling factor, in response to movement of said external power supply to maximize said increase.

A method, further comprising the step of increasing the amount of transferred energy to the internal power supply until a response of said coupling factor is detected.

A method, further comprising the step of indicating a positive or negative change in the coupling factor.

A method, further comprising the step of indicating an optimal placement of said second coil in relation to said first coil to optimize said coupling factor.

A method, further comprising the steps of:
analyzing the amount of energy being transmitted,
receiving feedback information related to the amount of energy received in the receiver, and
determining a value of the electromagnetic coupling such as the coupling factor by evaluating/comparing the amount of transmitted energy and the feedback information related to the amount of received energy.

A method, further comprising the step of generating a signal indicative of the coupling factor.

A method, further comprising the step of indicating displaying the feedback information or information derived therefrom.

A method, wherein the displayed information is displayed by a number of differently colored light sources.

A method of operating a device apparatus comprising the steps of:
creating an opening in the skin of a mammal patient,
dissecting an area of the patient,
placing the internal power supply device within said area,
charging said internal power supply postoperatively and non-invasively by
wirelessly transmitting energy from an external power supply, wirelessly transmitting feedback information from the internal power supply out of the patient's body, said feedback related to the amount of received energy, and
comparing the received energy with the transmitted energy in the external power supply.

A method, wherein the step of comparing the energy includes comparing the coupling factor of the coils.

A method, comprising the step of moving said external power supply for maximizing said coupling factor.

A method, wherein the step of creating an opening in the skin comprises the steps of:
inserting a tube or needle into the patient's body,
filling the body through the tube or needle with a gas and thereby expanding a cavity within the patient's body,
inserting at least two laparoscopic trocars into said cavity,
inserting at least one camera through at least one laparoscopic trocar, and
inserting at least one dissecting tool through at least one laparoscopic trocar.

A system for supplying energy to an implanted medical device for implantation in a patient's body, comprising
an internal charger arranged to be implanted in the patient's body, the internal charger comprising a first coil,
an external charger arranged to wirelessly transmit energy to supply the internal charger with energy, the external charger comprising a second coil, and
a wireless feedback system arranged to transmit feedback information from the internal charger to the external charger, wherein the feedback information is related to the strength of an electromagnetic field generated by the external charger.

Fourth combination embodiments including passive RFID technology

A system for supplying energy to an implantable medical device when implanted in a patient's body, comprising
an internal charger arranged to be implanted in the patient's body comprising a first coil,
an external charger arranged to wirelessly transmit energy to supply the internal charger with energy, the external charger comprising a second coil, and
a wireless feedback system arranged to transmit feedback information from the internal charger to the external charger, wherein the feedback information is based on information from at least one Radio Frequency Identification, RFID, transmitter.

A system, wherein the feedback information is related to the strength of an electromagnetic field generated by the external charger.

A system, wherein the RFID transmitter is arranged to change identification in response to the received electromagnetic field.

A system, wherein the wireless feedback system comprises more than one RFID transmitter or receiver.

A system, further comprising a triangulation module for determining the position of the internal charger based on triangulation of the RFID transmitter/s/.

A system, wherein the external charger comprises a display arranged to display the feedback information or information derived therefrom.

A system, wherein the display comprises a number of differently colored light sources.

A method of supplying, to an implantable medical device when implanted in a patient's body, comprising an internal power supply arranged to be implanted in the patient's body comprising a first coil, energy from an external power supply comprising a second coil, the method comprising the steps of:
wirelessly transmitting energy to supply the internal power supply with energy, and receiving feedback information from the internal power supply by the external power supply, wherein the feedback information is based on information from at least one Radio Frequency Identification, RFID, transmitter.

A method, wherein the feedback information is related to the strength of an electromagnetic field generated by the external power supply.

A method, wherein the RFID transmitter identification is set in response to the received electromagnetic field.

A method, wherein the wirelessly transmitted feedback information is transmitted and/or received using more than one RFID transmitter and/or more than one RFID receiver.

A method, further comprising the step of determining the position of the internal power supply based on triangulation of the RFID transmitter/s/.

A method, further comprising the step of indicating or displaying the feedback information or information derived therefrom.

A method, wherein the feedback information is displayed using a number of differently colored light sources.

A method of using a system or device, comprising the steps of:
creating an opening in the skin of a patient,
dissecting an area of the patient,
placing the internal power supply device within said area,
charging said internal power supply postoperatively and non-invasively by
wirelessly transmitting energy from an external power supply, said internal power supply further comprising a RFID identification,
wirelessly receiving feedback information from the internal power supply out of the patient's body as said RFID identification.

A method, further comprising the step of moving said external power supply, for maximizing said RFID identification, and optimizing the placement of said external power supply in relation to said internal power supply based on a maximized RFID identification.

A method, wherein the step of creating an opening in the skin comprises:
inserting a tube or needle into the patient's body,
filling the body through the tube or needle with a gas and thereby expanding a cavity within the patient's body,
inserting at least two laparoscopic trocars into said cavity,
inserting at least one camera through at least one laparoscopic trocar, and
inserting at least one dissecting tool through at least one laparoscopic trocar.

The system, wherein the first implantable coil is adapted in one embodiment to be placed subcutaneously, having a large diameter and adapted to be flexible enough for following patients movements, due to the helical structure of the coil wire.

The system, wherein in one embodiment the diameter of the first coil is large enough to allow a charging coil with large diameter to be placed in the bed of the patient, allowing recharging when the patient is asleep.

In yet another embodiment, the system comprises two or more implantable flexible first coils to allow a charging coil with large diameter to be placed in the bed of the patient, allowing recharging when the patient is asleep in different positions in the bed, charging different implantable first coils depending on the patient's position.

The system, wherein in another embodiment the two or more first coils are adapted to be placed at one or more of the following positions within the patient's body: abdominal wall outside, abdominal wall inside, pelvic area, the back, thoracic area, subcutaneously, thorax, abdomen, leg, arm, shoulder, and any other position in the body.

The system may comprise a charging feed back system for determining during the patient's sleeping time if the position of a first coil compared to a coil placed in the patient's bed allows recharging when the patient is asleep.

The system may have the diameter of the first coil being more than 0.5 cm or more than 10 cm or more than 15 cm or more than 2 cm or more than 1 cm or more than 30 cm or more than 5 cm.

The system may have the area of the first coil being more than 0.5 cm2 or more than 2 cm2 or more than 10 cm2 or more than 100 cm2 or more than 300 cm2 or more than 500 cm2 or more than 800 cm2.

A method for supplying energy to a medical device implanted in a mammal patient, the method comprising the steps of:

implanting a first coil according to claim 1,
placing a second coil external to the patient's body transmitting wireless energy to the first coil, implanted in the patient's body, wherein the first coil,
receiving wireless energy for
supplying energy or control signals to the medical device,
Wherein the first coil is wound from wire formed into a plurality of third coils connected to one another. Another method for implanting and energizing a medical implant comprises the method steps of:

implanting a receiver according to claim 38, in a mammal patient's body, the receiver
receiving energy from an external energizer transmitting wireless energy to said receiver,
supplying the medical implant apparatus with energy, wherein the receiver comprises an internal coil, the internal coil comprising first and second coil windings perpendicular to each other, wherein the first coil windings each have a diameter that is smaller than the second coil winding's diameter.

Yet another method of charging an implant, wherein the diameter of the first coil is large enough,
allowing a charging coil with large diameter to be placed in the bed of the patient, and
allowing recharging when the patient is asleep,
The method may involve two or more implantable flexible first coils,
allowing a charging coil with large diameter to be placed in the bed of the patient,
allowing recharging when the patient is asleep in different positions in the bed, and
charging different implantable first coils depending on patient position.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

FIGS. 8a and 8b are schematic views of a chargeable medical device,

FIG. 9 is a schematic view illustrating the operation of a charger system,

DETAILED DESCRIPTION OF THE INVENTION

In this description, the term "coil" refers to an arrangement having at least one winding. When reference is made to the sizes of coils, it is meant the internal area of the coil as seen from one end thereof.

Figure 1:
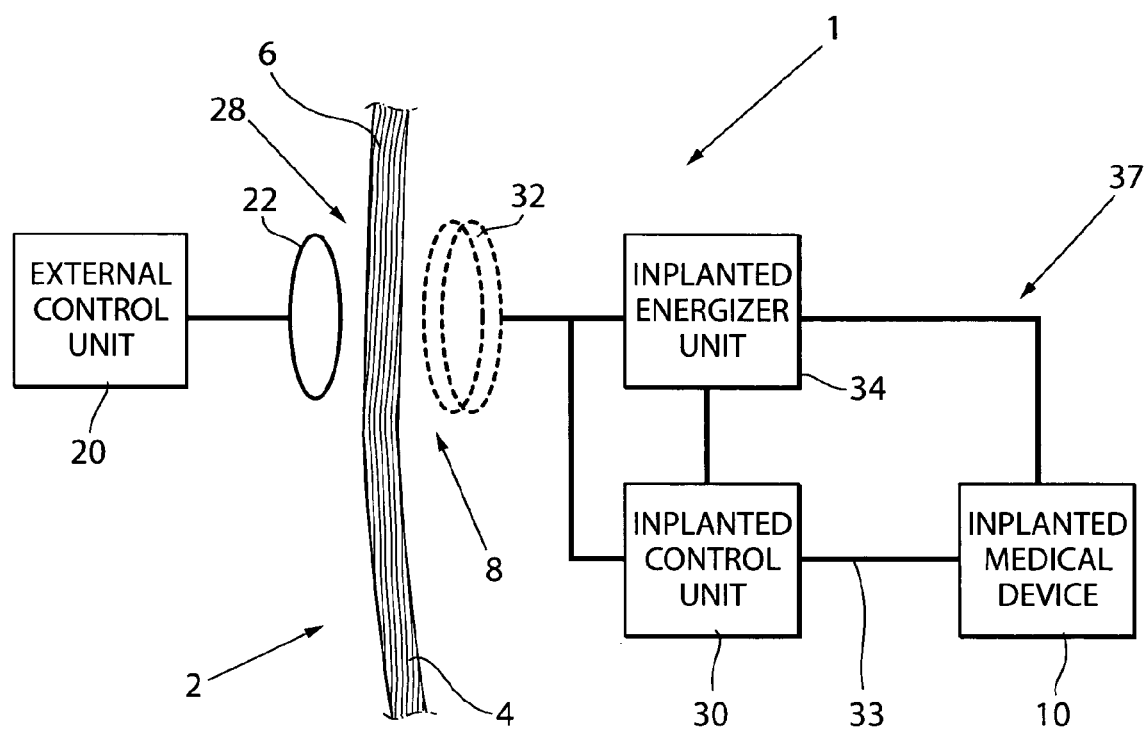
FIG. 1 is a schematic diagram of a system using the improved coil of the present invention to supply energy or control signals to, or information from, a medical device implanted in a human or animal patient's body.

FIG. 1 is a schematic diagram of a system 1 using the improved coil 32 of the present invention to supply energy or control signals to, or information from, a medical device 10 implanted in a human or animal patient's body. FIG. 1 shows the basic parts of the system 1. All parts placed to the left of the patient's skin 4 are located outside of the patient's body and all parts placed to the right of the skin 4 are implanted in the patient's body.

The system 1 includes a pair of coils 22 and 32 that function as inductively coupled electrical conductors forming a transformer like circuit for the purpose of transferring alternating electrical energy signals into and out of a patient's body that supply energy or control signals to, or information from, the medical device 10 implanted in the patient's body 6.

The coil arrangement of the present invention has many similarities with a transformer. A transformer is an electrical device that transfers electrical energy from one circuit to another circuit through inductively coupled electrical conductors formed into coils. An alternating current in a first winding or circuit of the transformer, often called the primary circuit, creates an alternating magnetic field, which induces an alternating voltage in a second winding or circuit of the transformer, often called the secondary circuit. An electric charge then flows in the secondary winding or circuit to a load circuit connected to the secondary circuit, so as to transfer energy from the primary circuit through the secondary circuit to the load circuit connected into secondary circuit.

The system 1 includes an external control unit 20 located outside of the patient's body. The external control unit is comprised of a generator for generating an alternating electromagnetic signal, a modulator circuit and a power amplifier. The external control unit 20 may include a microprocessor for generating control signals to be sent to the implanted medical device 10. The microprocessor is capable of switching the generator on and off and of controlling the modulator circuit to modulate signals generated by the generator to send control information to the implanted medical device 10 via the power amplifier and a transmitting coil 22 connected to the power amplifier in the external control unit 20. Where the external control unit 20 is a transceiver that functions to both transmit control signals to the implanted medical device 10 and receive information signals from the implanted medical device 10, the external control unit 20 also includes a demodulator that is also connected to external coil 22, which receives the information sent from the implanted medical device 10. The demodulator demodulates information signals received by the external coil 22 so as to strip out the information sent from the implanted medical device 10. Typically, such information will relate to bodily functions being monitored by the implanted medical device or the results of bodily functions controlled by the implanted medical device.

Implanted in the patient's body is an implanted control unit 30, which is connected to the implanted coil 32. Where the implanted coil 32 is used to supply energy to the implanted medical device 10, the implanted control unit 30 will include a rectifier circuit for converting alternating signals received by the coil 32 into a direct current signal that is suitable for either powering the operation of the implanted medical device 10 or charging an implanted rechargeable energizer unit 34 that powers the operation of the implanted medical device 10.

Where the implanted coil 32 is used to receive control signals from the external control unit 20 and to transmit information signals from the implanted medical device 10 to the external control unit 20, the implanted control unit 30 will be further comprised of a demodulator and a microprocessor. The demodulator demodulates signals sent from the external control unit 20. The microprocessor receives the demodulated signal and sends control signals via a control line 33 to the implanted medical device to control its operation.

Where the implanted control unit 30 is a transceiver that functions to both receive control signals from the external control unit 20 and transmit information from the implanted medical device 10, the implanted control unit 30 will also include a generator for generating an alternating electromagnetic signal, a modulator circuit for modulating the generated alternating electromagnetic signal and a power amplifier connected to the implanted coil 32. The microprocessor is capable of switching the generator on and off and of controlling the modulation circuit to modulate the signals generated by the generator to send information from the implanted medical device 10 via the power amplifier and implanted coil 32 connected to the power amplifier to the external control unit 20.

Figure 2A:
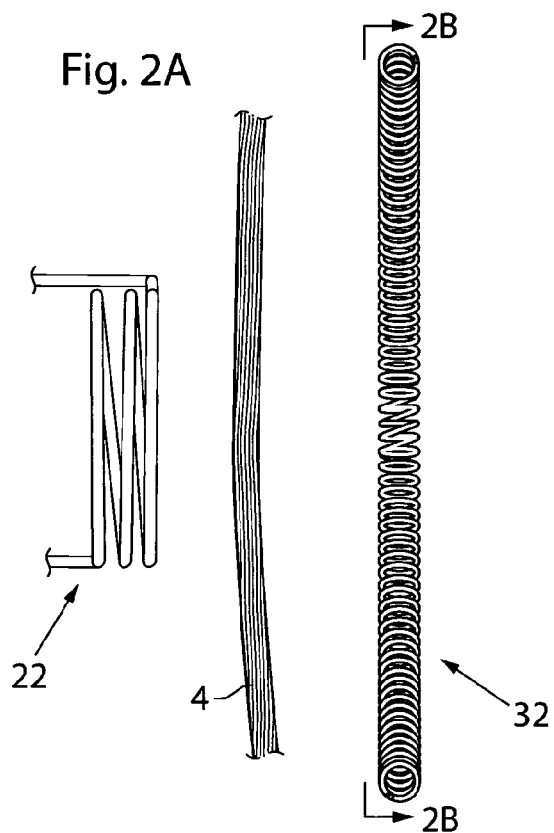
FIG. 2A is a schematic diagram of the coil arrangement of the present invention implanted inside a patient's body showing an external coil that is located outside of the patient's body and that is inductively coupled to a coil implanted in the patient's body.

FIG. 2A is a schematic sectional diagram of the implanted coil 32 of the present invention implanted inside a patient's body and another coil 22 inductively coupled to the implanted coil 32 that is located outside of the patient's body and separated by the patient's skin 4.

Figure 2B:
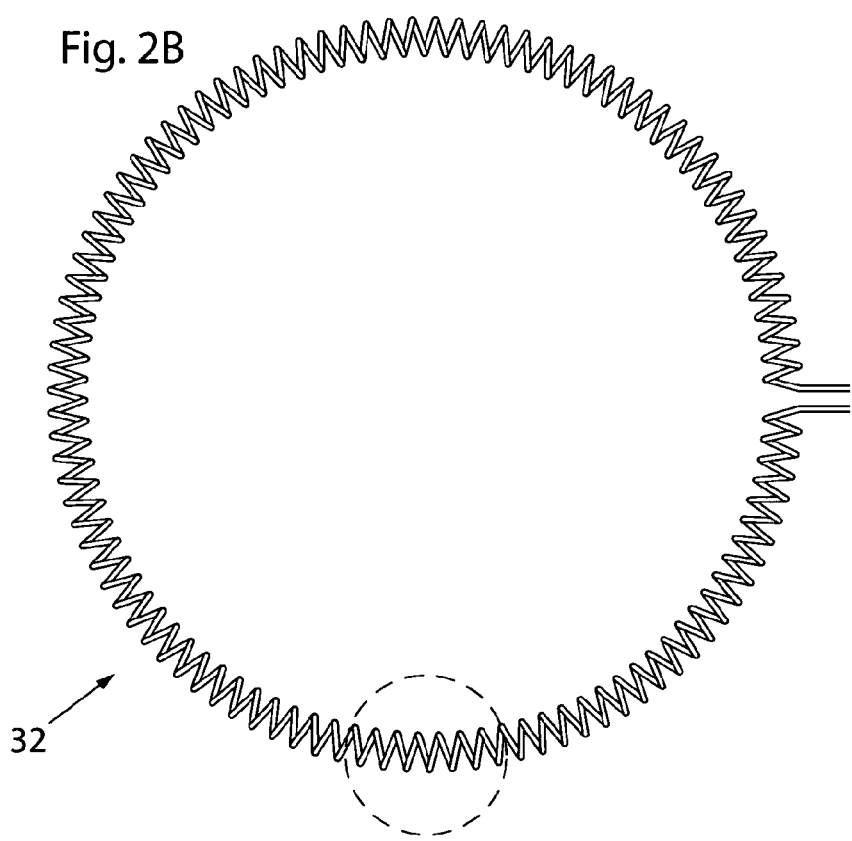
FIG. 2B is a plan view of a coil implanted in the patient's body.

FIG. 2B is a plan view of the implanted coil 32 as seen in the direction from outside the patient. In this embodiment, the coil comprises one single large winding, the ends of which are connected to the medical implant.

Figure 2C:
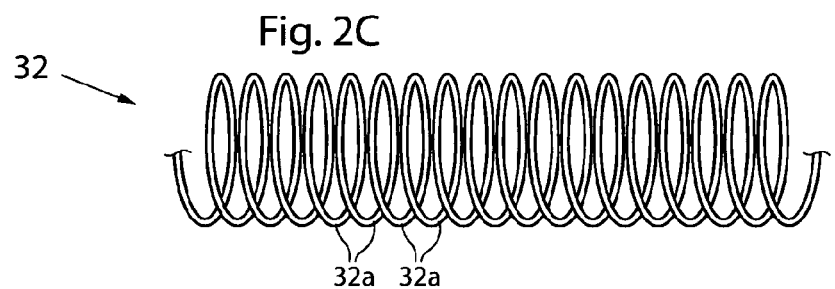
FIG. 2C is a detailed view of the coil shown in FIG. 2B, showing the helically-shaped wire forming the improved coil of the present invention that is used in the system shown in FIG. 1.

As can be seen from FIG. 2C, the implanted coil 32 is formed from a wire that is formed into a plurality of smaller diameter coils or windings 32a that are connected in series. As can be seen from FIGS. 2B and 2C, as the wire is wound to form the implanted coil 32, the smaller diameter coils or windings 32a are caused to be positioned substantially perpendicular to the longitudinal axis of implanted coil 32. As can also be seen from FIG. 2B, preferably the wire is a helically-shaped wire that is very resilient, and, thus, capable of handling even extreme movements of a patient 2 in whom it is implanted without the risk of breaking.

Figure 2D:
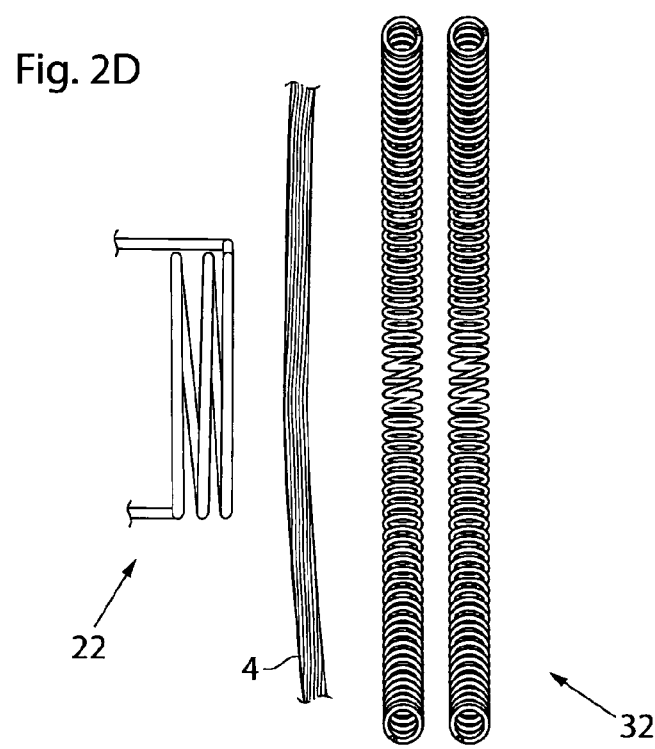
FIG. 2D is a view similar to that of FIG. 2B but showing the implanted coil with a plurality of windings, in the shown embodiment two windings.

FIG. 2D is a diagram similar to that of FIG. 2A but showing an implanted coil 32 comprising a plurality of large windings, in the shown embodiment two large windings, each of the large windings being made up of a plurality of small diameter coils or windings.

Figure 2E:
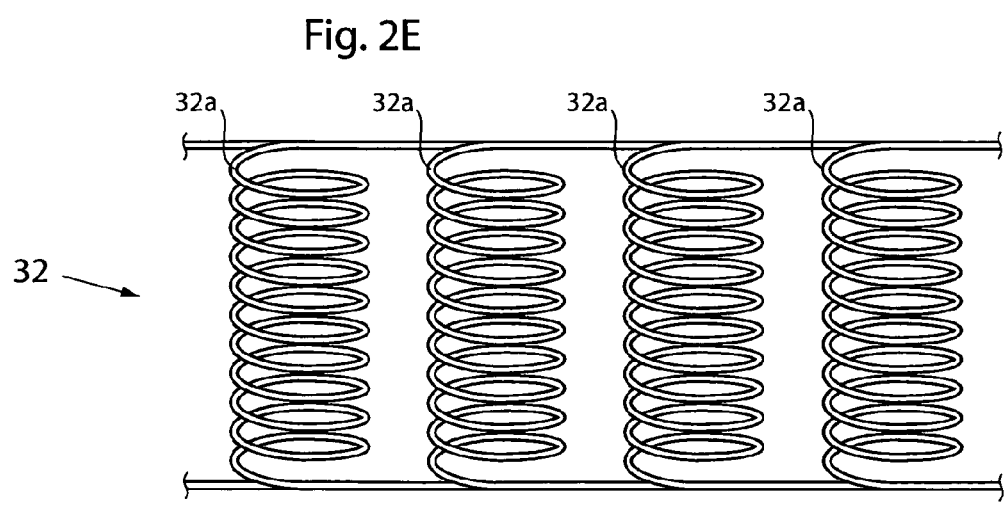
FIG. 2E is a detailed view of another embodiment of the coil shown in FIG. 2B, wherein the implanted coil comprises a plurality of coils connected in parallel.

FIG. 2E is a detailed view of another embodiment of the coil shown in FIG. 2B, wherein the implanted coil 32 comprises a plurality of coils connected in parallel.

Figure 3:
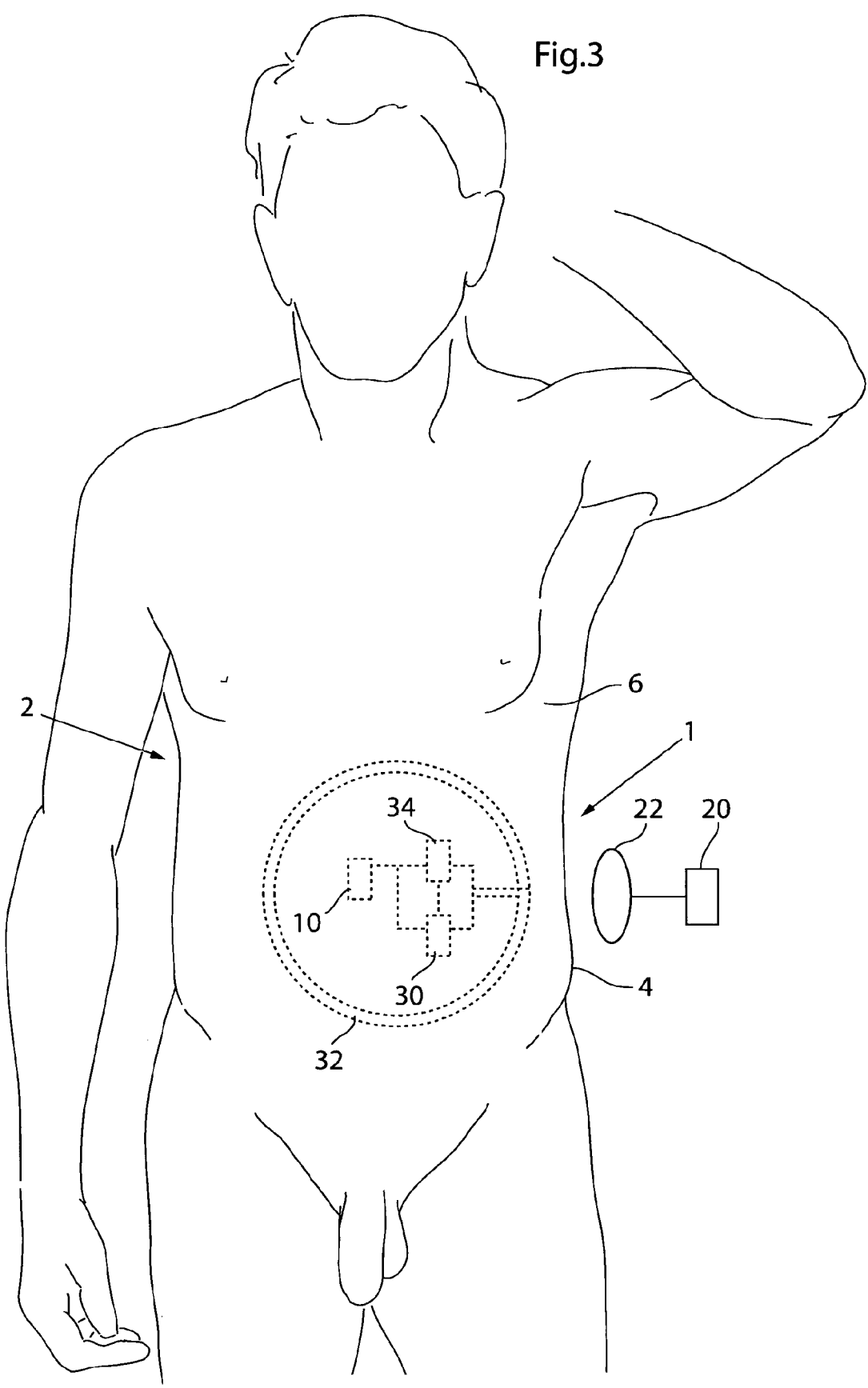
FIG. 3 is a schematic diagram showing the coil of FIG. 2B and the apparatus of FIG. 1 implanted in the body of a human patient.

FIG. 3 is a schematic diagram showing the implanted coil 32 of FIGS. 2A-2D and the system 1 of FIG. 1 implanted in the body 6 of a human patient 2. As shown in FIG. 3, the implanted coil 32 is implanted in the body 6 of patient 2 at a location that permits easy access to the coil 32 from outside of the patient's body 6. Preferably, the coil 32 is implanted subcutaneously in the skin 4 of the patient 2 at a location for such easy access. Preferably, the implanted control unit 30 and the rechargeable energizer unit 34 are also located at an easy access location within the body 6 of the patient 2 and then connected by one or more wires to the implanted medical device 10.

From FIG. 3 it is seen that the implanted coil 32 can take an irregular shape, adapting to the patient's body. Therefore, the implanted coil 32 can be made very large, preferably much larger than the external coil 22, and covering a large portion of the patient. This could allow for charging for example when the patient is in bed if an external coil 22 is provided in the bed structure.

The implanted coil can be implanted either in the stomach area or the back area of the patient.

It should be noted that FIGS. 1, 2A-2D and 3 are not intended to depict a particular orientation of the external coil 22 and/or the implanted coil 32 with respect to a patient with whom these devices are used. Rather, it should be noted that either or both of these devices can be oriented horizontally, vertically or otherwise with respect to a patient to accommodate the needs of a particular application in which these devices are used. Furthermore, the coil winding itself could be done any one of many different ways. Preferably, the coil winding is compact with the windings concentrated in a small transversal area. A core could also be used with the coil, but it is not required. If such a coil were to be implanted in a patient with a substantially horizontal orientation vis-à-vis the substantially vertical orientation of the patient, when standing, the coil would preferably be very low in subcutaneous height, thereby avoiding protruding material under the skin.

Figure 4:
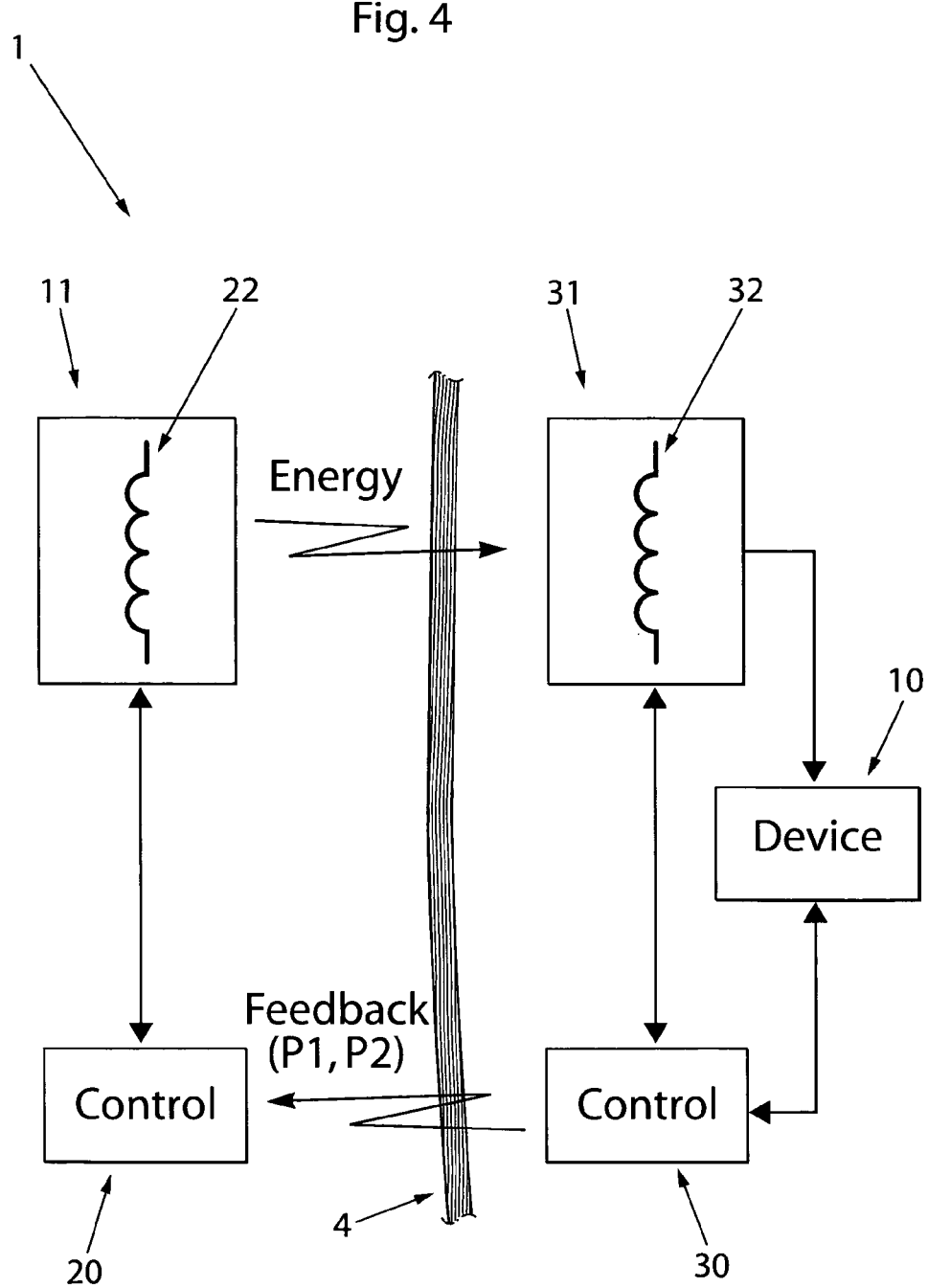
FIG. 4-7 show circuit diagrams.

FIG. 4 shows a schematic view of an embodiment of a medical system 1 of the invention. As shown, the medical system 1 comprises parts intended for implantation in a patient as well as external parts intended to be used outside of the body of the patient in whom the internal parts are implanted. FIG. 4 shows the skin of a patient symbolically with a line "4", in order to show how the system is divided into external and internal parts. The external parts comprise an external energy source 11 equipped with a primary external coil 22 for transmitting energy wirelessly by means of induction to an internal energy receiver 31. Also comprised in the external parts is a control unit 20 for controlling, inter alia, the external energy source 20 and its function.

The internal parts of the system 1 comprise a medical device 10, the internal energy receiver 31 and an internal control unit 30. The medical device 10 is electrically powered, and as indicated by the name, the purpose of the internal energy receiver 31 is to receive energy and to supply that energy to the medical device 10. The energy which the energy receiver 31 receives for the medical device is received wirelessly, by means of induction, for which reason the energy receiver is equipped with a secondary implanted coil 32 for receiving such energy. A purpose of the internal control unit 30 is to control the internal parts.

As shown in FIG. 4, the internal control unit 30 is arranged to wirelessly transmit feedback information regarding, for example, the transfer of energy to the internal energy receiver 31, and as indicated in FIG. 4, the feedback information is based on or relates to a first and a second parameter, P1, P2.

Regarding the nature and function of the medical device 10, the invention is applicable to a large number of implantable medical devices, for which reason the medical device is only referred to by the generic term "medical device". However, examples of implantable electrically powered medical devices in which the present invention can be applied are devices which aid patients who suffer from urinary dysfunction, intestinal dysfunction, infertility, impotence, vascular and heart related diseases, reflux disease, obesity etc. The invention can also be used to assist patients with food passageway correlated devices, implanted drug delivery, drainage, etc.

A purpose of the present invention is to enable a more rapid adjustment of the energy which is transferred to the implanted medical device 10, so that the energy which is transferred better corresponds to the needs of the medical device 10. To this end, the system 1 is arranged to determine the feedback information based on or relating to the first and second parameters P1, P2.

The system 1 is arranged to determine a balance between the amount of energy received in the energy receiver and the amount of energy used by the medical device, and to determine the first parameter P1 being based on this energy balance over a certain amount of time. The energy balance can either be specified as the balance between the total amount of energy received in the energy receiver and the amount of energy used by the medical device or as the balance between the rate of energy received in the energy receiver and the rate of energy used by the medical device. The amount of time over which the balance is determined is a design parameter which is adapted to the specific needs of each system and application, and may thus vary, but is suitably in the range of 50-200 ms, although the invention covers any range of time. In addition, the amount of time over which the balance is determined is suitably chosen to coincide with the feedback information, which is thus also suitably transmitted at intervals of 50-200 ms, or more often or more seldom.

The second parameter, P2, is based on information which relates to a coupling factor between the external coil 22 and the implanted coil 32. The intervals of time at which this coupling factor is determined is a design parameter which is adapted to the specific needs of each system and application, and may thus vary. The coupling factor can also be used as a calibration parameter which is determined much more rarely than the energy balance or it may also be simultaneously controlled. However, the second parameter P2 will normally not change since it is related to the coupling factor, if the external coil is kept stationary.

The system 1 is adapted to take into account at least both the first P1 and the second P2 parameter in order to determine the amount of energy which should be transmitted by the external energy source 11, which will enable a rapid adjustment of said energy balance. The manner in which the system takes these parameters into account can vary, but a number of ways will be described below.

In one embodiment, the energy balance mentioned previously is determined by the internal control unit 30, suitably by means of a processor in cooperation with a memory in the control unit, by means of retrieving the data necessary for establishing the balance over the period of time in question. Thus, the processor checks the energy received by the energy receiver and the energy consumed by the medical device, and determines the balance.

In addition to this, in this example of an embodiment, the second parameter P2 is also determined by the internal control unit 30, suitably by the processor and the memory mentioned above. As mentioned, the second parameter P2 relates to the coupling factor between the external coil 22 in the external energy source 20 and the implanted coil 32 in the internal energy receiver 31, suitably as seen over a certain interval of time. Suitably but not necessarily, the second parameter P2 is the coupling factor.

Thus, in such an embodiment, the internal control unit 30 needs information from the external control unit 20 in order to determine the coupling factor. This information is supplied to the internal control unit 30, suitably wirelessly, by the external control unit 20, and the internal control unit 30 then determines the coupling factor.

When the internal control unit has the coupling factor and the balance, it has both of the parameters P1 and P2, and can then determine the amount of energy which should be transmitted by the external energy source 20 in order to achieve an adjustment of the energy balance towards a desired figure. For example, if the desired figure for the balance is 98%, and the balance has been determined to be 85%, an increase is necessary. If the coupling factor has been determined to be ideal, i.e. 100%, the necessary increase is less than it would have been with a coupling factor of, for example, 50%.

Thus, taking the coupling factor and the balance into account, the internal control unit arrives at a conclusion regarding the "sign" of a change in the amount of energy which should be transmitted, so that an increase has a positive sign, "+", a decrease has a negative sign, "−", and a "steady state" is without sign. The change (if any) is then transmitted to the external control unit 20 as a combination of a sign and a number signifying a percentage, e.g. "+15", "−30", "0", etc, where they are interpreted and acted upon correspondingly by the external control unit 20. In this embodiment, the internal control unit 30 is thus arranged to transmit information wirelessly to the external control unit 20, suitably by means of radio transmission, although other means of wireless transmission can also be used within the scope of the present invention, such as, for example, ultrasound.

In further embodiments of the system of the invention, there is also a third parameter P3, which is used by the system.

Suitably, in those embodiments of the system in which there are three parameters, all three parameters are used by the system in order to determine the feedback information, and the feedback information comprises information comprising or relating to the amount of energy which should be transmitted by the external energy source.

In one embodiment of the invention, the system is adapted to use the second and third parameters for determining the amount of energy which should be transmitted by the external energy source, and to use the first parameter during operation of the system in order to determine the amount of energy which should be transmitted by the external energy source during operation of the system. Thus, the second and third parameters are used when initializing the system, for example when turning the system on, in conjunction with which the necessary energy level needs to be established, which may also need to be done at sparse intervals during operation of the system. However, in this embodiment, the first parameter is used to regulate the energy level, i.e. to see to it that the energy transmitted during operation of the system is on the level which has been established using the second and third parameters, so that the first parameter is used in order to "tune" the transmission of energy during operation of the system.

Figure 5:
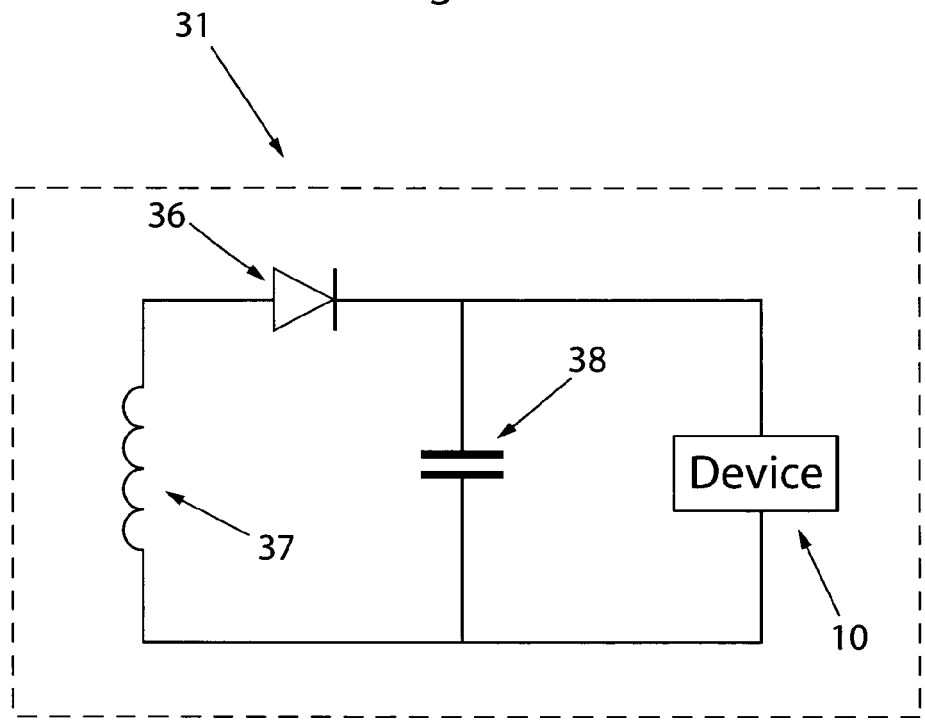

In one such "three parameter embodiment", which will be described with reference to FIG. 5, the system comprises a capacitor 38 coupled to the implanted coil 32. As shown in FIG. 5, the capacitor 38 is suitably arranged in the energy receiver 31, and is arranged in parallel with the implanted coil 32. Also, as shown in FIG. 5, in one embodiment the secondary coil is connected to the medical device 10 via a half wave rectifier, here shown as a diode 36, and the capacitor 38 is connected in parallel to the implanted coil 32 with the half wave rectifier between the capacitor and the implanted coil 32.

The capacitor 38 will, due to the design shown in FIG. 5, store energy when there is a voltage over the implanted coil 32, the amount of energy, "E", being defined by the expression $E=(V*Q)/2$, where V is the voltage over the capacitor and Q is the charge on each plate of the capacitor.

In the embodiment with the capacitor 38, the system of the invention is arranged to determine the total amount of energy, "E", stored in the capacitor 38, and the third parameter P3 comprises or is based on the total amount of energy, "E", stored in the capacitor, and the system is adapted to take into account the third parameter P3 in order to determine the amount of energy which should be transmitted by the external energy source. For example, if E is above a certain threshold value, this could be taken by the internal control unit 30 as an indication that the amount of energy to be transferred could be lowered or at least maintained at the same level, and if E is below the threshold value, this could be seen by the internal control unit 30 as an indication that the amount of energy to e transferred should be increased. Thus, it is suitably the internal control unit 30 that monitors the level of energy stored in the capacitor 38, and determines the third parameter P3.

In a further "three parameter embodiment", schematically illustrated in FIG. 5, the medical device 10 also comprises a regulator 39 either a current regulator or a voltage regulator, which is thus arranged to keep a current or a voltage in the medical device constant. In such an embodiment, the system is arranged to determine a difference between an input voltage/current to the voltage/current regulator and the voltage or current which the regulator is arranged to keep constant.

In this embodiment, the system bases the feedback information from the internal control unit to the external control unit on a third parameter P3 parameter which comprises or is based on this voltage/current difference. The system is thus adapted to also take into account the "regulator" parameter P3 when determining the amount of energy which should be transmitted by the external energy source.

Figure 6:
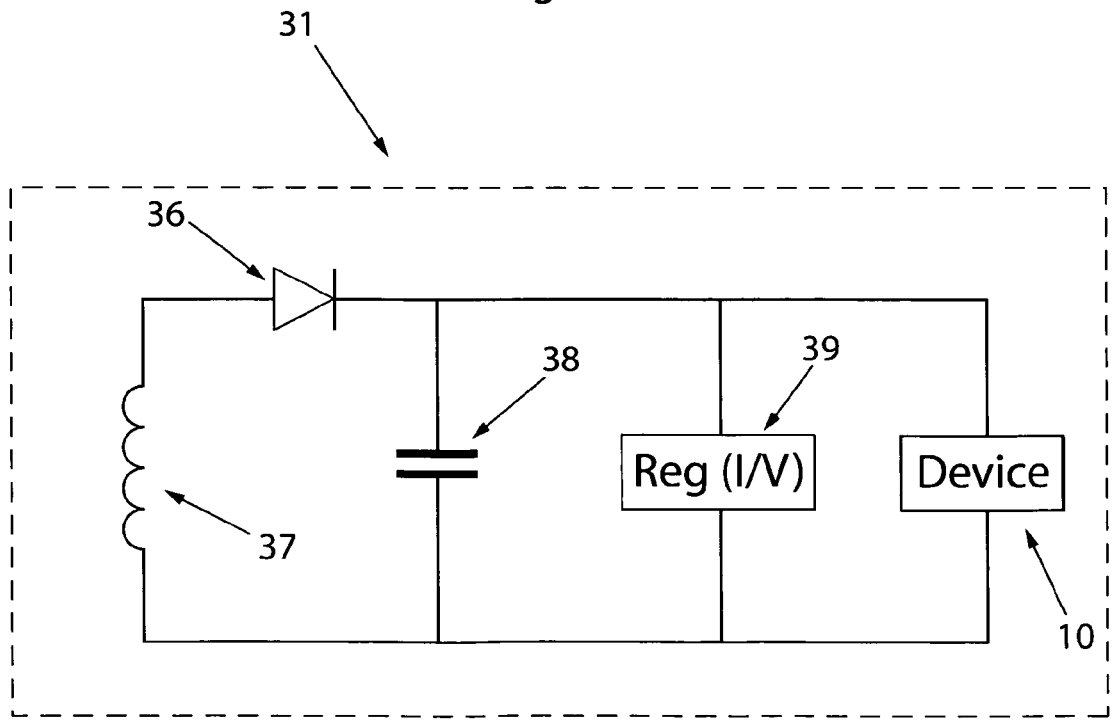

As shown in FIG. 6, the regulator 39 is in one embodiment a voltage regulator arranged to measure the voltage V over the medical device 10, as an alternative to which it can also be a current regulator arranged to measure the current I to the medical device 10.

In one embodiment, the system of the invention will further comprise an indicator in the external energy source, adapted to indicate a level of the coupling factor between the external coil 22 and the internal implanted coil 32. In such an embodiment, the same or another indicator in the external energy source is suitably used for indicating an optimal placement of the external coil 22 in relation to the implanted coil 32 in order to optimize the coupling factor.

Figure 7:
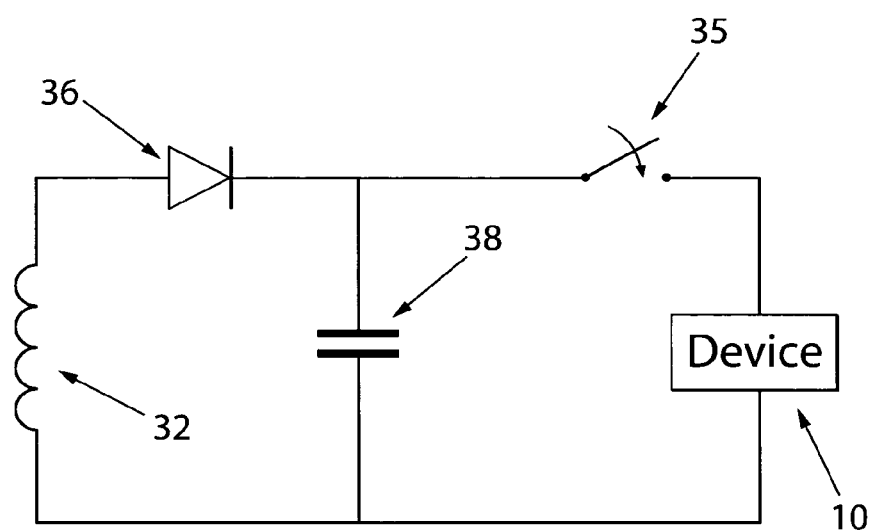

As shown in FIG. 7, in one embodiment of the system of the invention, the energy receiver comprises a switch 35 which is adapted to switch a connection between the implanted coil 32 and the medical device 10 on and off, in order to enable the system to measure the coupling factor when the connection is off. Suitably, the internal control unit 30 handles the control of the switch 35.

In a further embodiment, the energy receiver 31 comprises an electronic component which is connected to the secondary coil for preventing the flow of electrical current between the implanted coil 32 and the medical device 10 during measurement of parameters, for example parameters related to related to the coupling factor. These measurements are suitably carried out by the internal control unit 30, and in one embodiment the electronic component is the diode 36 which has been described previously. Thus, measurements can be carried out either when the diode is biased by the voltage caused by the inductive voltage over the implanted coil 32, or the control unit can cause the diode to be biased to block current to the medical device 10. If the diode 36 "blocks" the connection between the implanted coil 32 and the medical device 10, the implanted coil 32 will be substantially without an electrical load when the coupling factor is measured, which is beneficial for obtaining a good measurement result.

In one embodiment, the external energy source 20 comprises an electronic circuit (not shown) for comparing the feedback information with the amount of energy transmitted by the external energy source. Also, alternatively, this electronic circuit may be comprised in the control unit 20.

In a further embodiment, the system also comprises an internal control unit, preferably the internal control unit 30, which is adapted to determine the energy balance between the energy received by the energy receiver 31 and the energy used by the medical device 10; in this embodiment the system also comprises an external control unit such as the control unit 20 which is adapted to calibrate the transmission of wireless energy from the external energy source 11 using feedback information.

In one embodiment, the system of the invention comprises at least one energy stabilizing unit in or connected to the medical device 10, arranged to stabilize received energy prior to use by the medical device 10.

In FIG. 8a another view of a chargeable medical system is depicted. The system comprises an implanted coil 32 implanted in a patient. The implanted coil 32 is adapted to receive wireless energy from an external coil 22 through the skin 4 of the patient in accordance with the above. The internal charger is connected to an internal energy supply such as a battery 30. The internal energy supply supplies energy used for driving an implanted medical device 10. The implanted medical device 10 can be operated using a mechanically or hydraulically controlled control device. For example the implanted medical device can be adapted to mechanically or hydraulically adjust a member 108 located in conjunction with a blood vessel 112 or some other internal organ 112 for controlling the flow in the vessel or organ 112. In FIG. 8a the member 108 is mechanically or hydraulically adjusted to a generally closed position.

In FIG. 8b another view of the chargeable medical device 10 is depicted. The view in FIG. 8b corresponds the view in FIG. 8a but with the member 108 mechanically or hydraulically adjusted to a generally open position.

In FIG. 9 a view further illustrating the operation of a charger system as described herein. Hence in order to find an optimal position of the external control unit 20 for transferring energy to the implanted coil 32, the external control unit 20 is moved of the skin of the patient. In response to feedback information from the implanted medical device the optimal position for charging the implanted medical device is selected. The operation is further described below in conjunction with FIG. 10.

Figure 10:
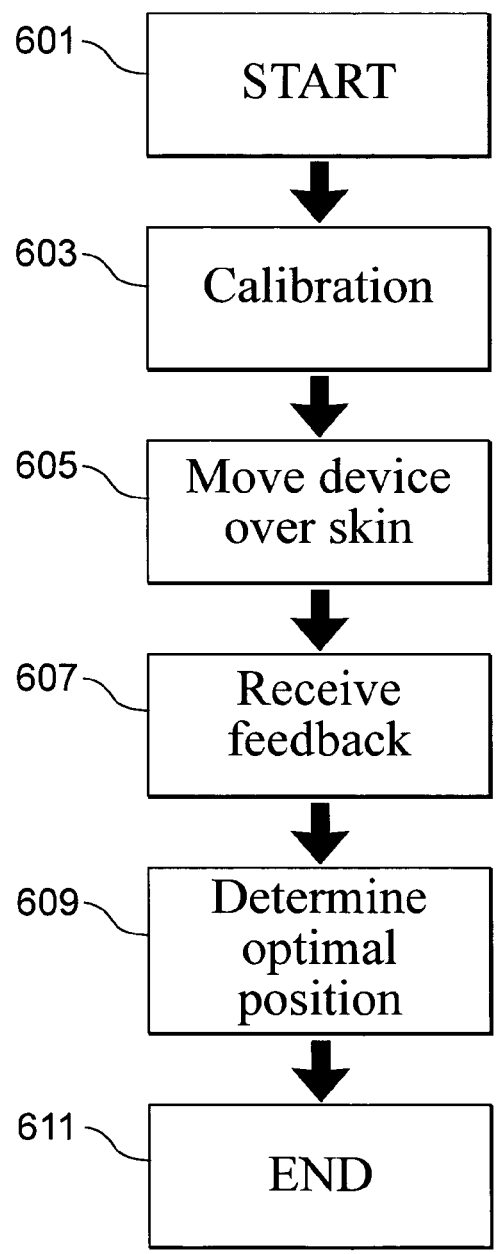
FIG. 10 is a flowchart illustrating the operation of a charger system.

In FIG. 10 a flow chart illustrating steps performed when using the system as described herein in order to find an optimal position for charging an internal charger for supplying power to an implanted medical device. First in a step 601 the external charger is turned on. Next in a step 603 the charger runs through a calibration procedure for producing a response from the internal charger. Next in a step 605 the user starts to move the external charger over the skin of the patient. Thereupon, in a step 607, the user receives feedback information from the system enabling the user to move the external charger to a more favorable position. Upon finding an optimal position the charger indicates that in a step 609 and the procedure ends in a step 611.

Figure 11:
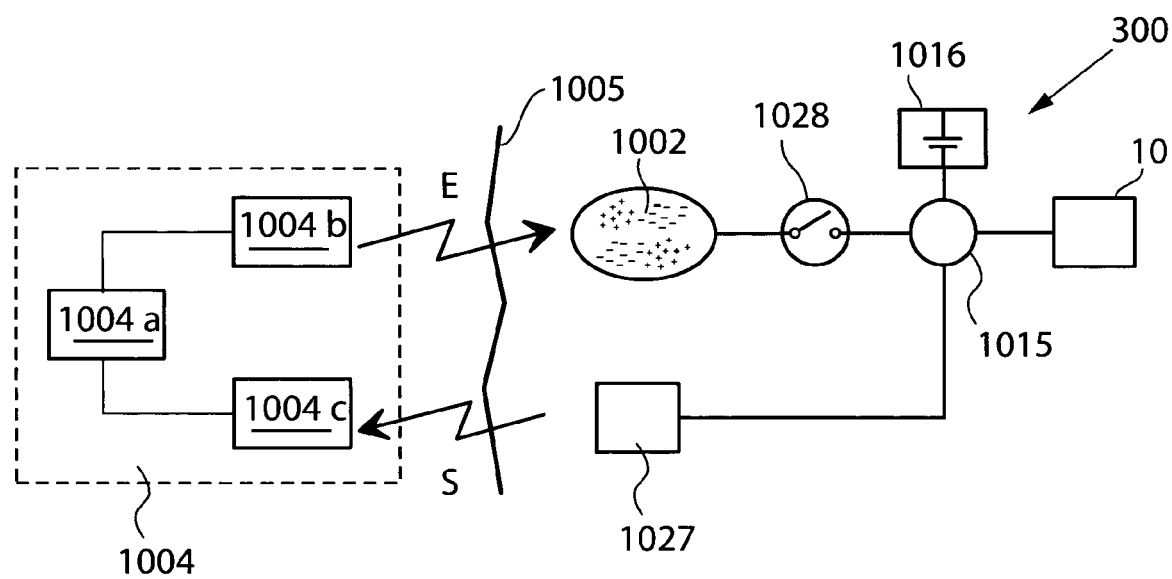
FIG. 11 is a schematic view of an implanted chargeable medical device.

In FIG. 11 another view of an implanted chargeable medical device 10 is depicted. Here, the patient's skin is indicated by a vertical line 1005. Here, the internal charger in the form of an energy receiver comprises an energy-transforming device 1002 located inside the patient. The energy receiver such as a coil can preferably be located just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from an external energy-source 1004a, in particular an external charger such as a coil provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between a switch 1026 and an implanted medical device 10. The internal control unit 1015 may thus be arranged to receive various measurements obtained by suitable sensors or the like, not shown, measuring certain characteristics of the implanted medical device 10, somehow reflecting the required amount of energy needed for proper operation of the implanted medical device 10. Moreover, the current condition of the patient may also be detected by means of suitable measuring devices or sensors, in order to provide parameters reflecting the patient's condition. Hence, such characteristics and/or parameters may be related to the current state of the implanted medical device, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the implanted medical device. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the implanted medical device 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the implantable medical device 10, or the patient, or an implanted energy source if used, or any combination thereof. The internal control unit 1015 can further be connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to an external signal receiver 1004c and the external control unit 1004*b*. The energy balance and the currently required amount of energy can then be determined by the external control unit 1004*b* based on those sensor measurements.

Hence, the system in accordance with the arrangement depicted in FIG. 11 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. The switch 1026 can either be separate and controlled by the internal control unit 1015, or integrated in the internal control unit 1015. It should be understood that the switch 1026 can be implemented by any type of suitable device such as a transistor, MCU, MCPU, ASIC FPGA or a DA converter or any other electronic component or circuit that may switch the power on and off.

The energy supply arrangement illustrated in FIG. 7 may in accordance with one embodiment be operated in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

The system as described herein above may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 12:
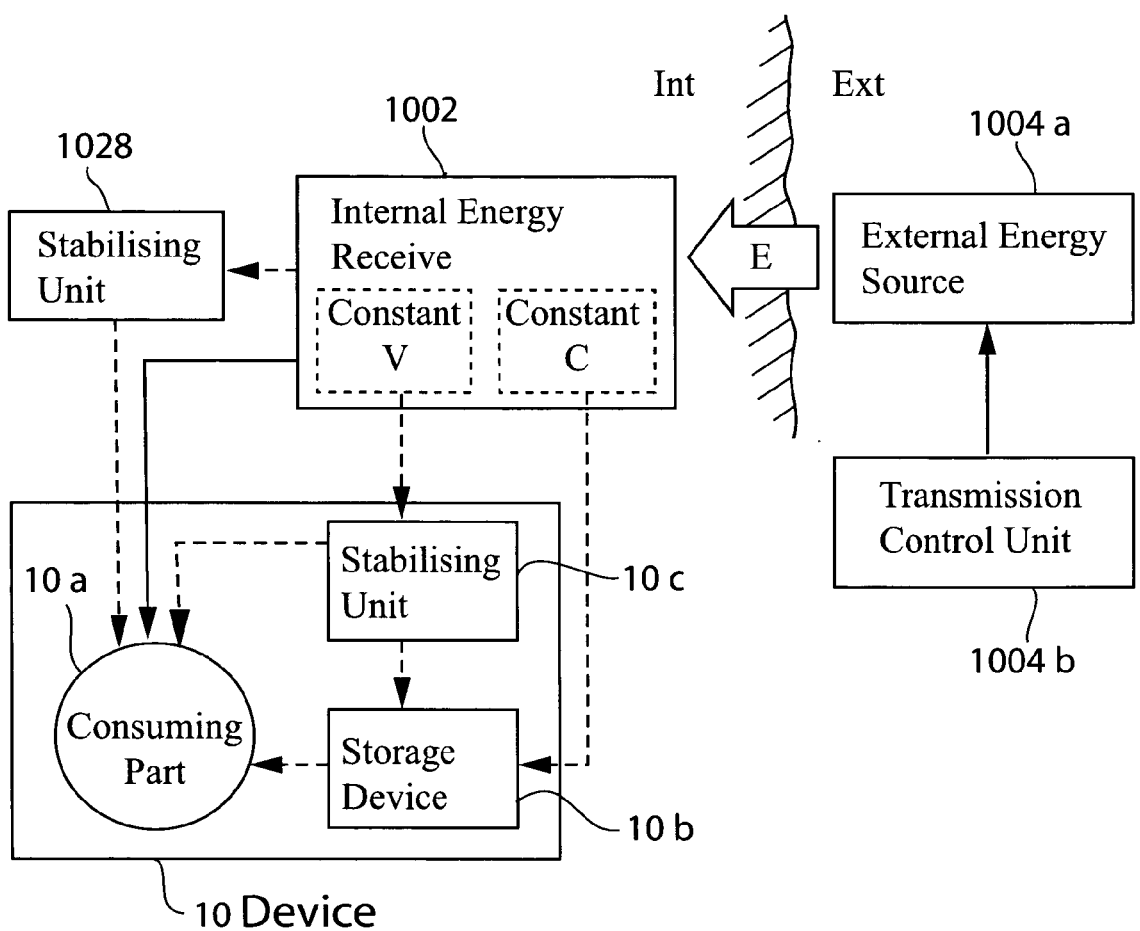
FIG. 12 is a schematic view of an implantable medical device.

FIG. 12 illustrates different embodiments for how received energy can be supplied to and used by the implantable medical device 10. Similar to the example of FIG. 11, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the implantable medical device 10. The internal energy receiver 1002 may further comprise a constant current circuit, indicated as a dashed box "constant C" in the figure, for supplying energy at constant current to the implantable medical device 10.

The implantable medical device 10 can comprise an energy consuming part 10*a* for example a motor, a pump, a restriction device, or any other medical appliance that requires energy for its electrical operation. The implantable medical device 10 may further comprise an energy storage device 10*b* for storing energy supplied from the internal energy receiver 1002. Thus, the supplied energy may be directly consumed by the energy consuming part 10*a*, or stored by the energy storage device 10b, or the supplied energy may be partly consumed and partly stored. The implantable medical device 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the implantable medical device 10, before being consumed and/or stored by the implantable medical device 10. Alternatively, the energy stabilizing unit 1028 may be integrated in the internal energy receiver 1002. In either case, the energy stabilizing unit 1028 may comprise a constant voltage circuit and/or a constant current circuit.

Figure 13:
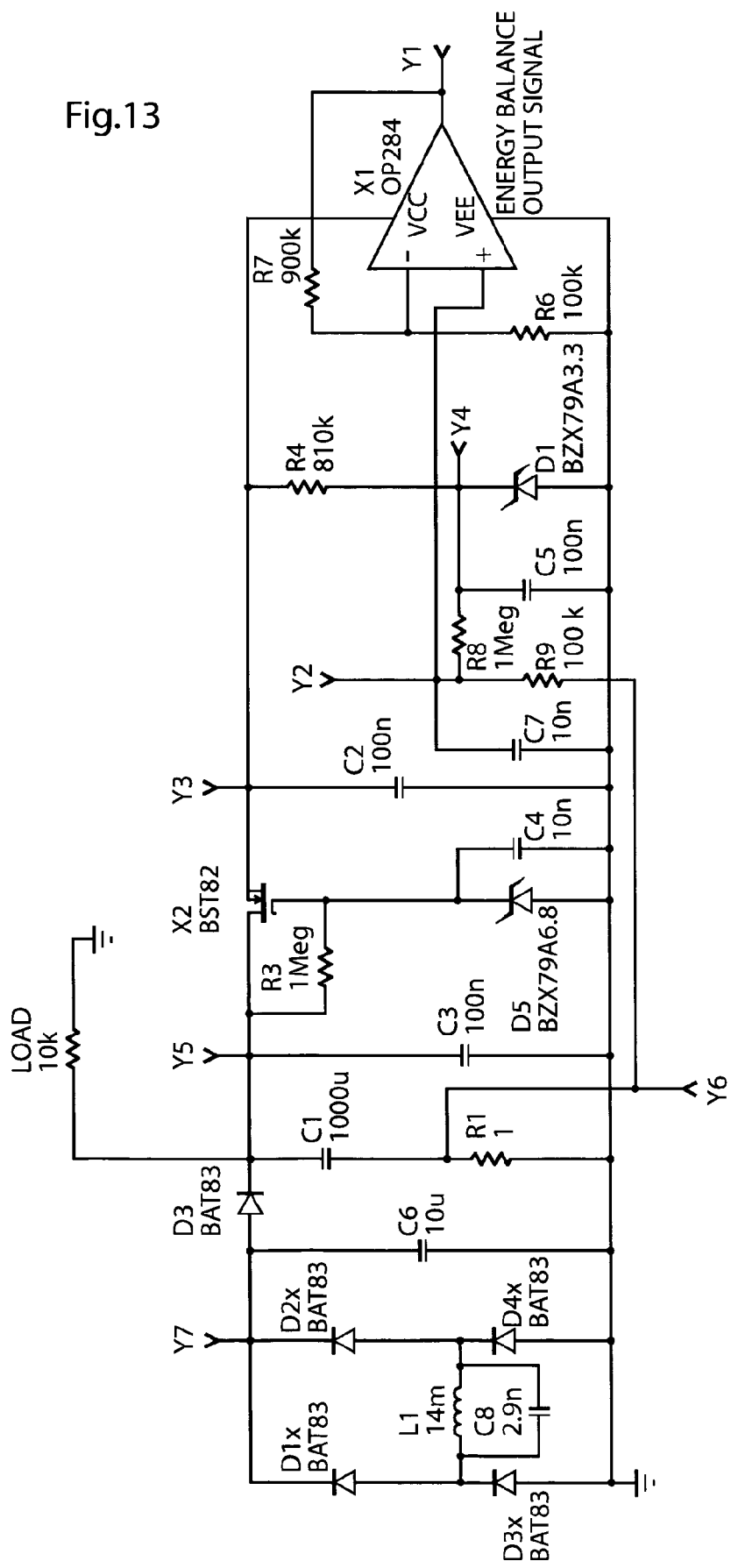
FIG. 13 is a circuit diagram of for a system for transferring energy to implanted components.

FIG. 13 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the device, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 13 shows a circuit implementation for a system that transfers energy to the implanted energy components of the device of the present invention from outside of the patient's body using inductive energy transfer. An inductive energy transfer system typically uses an external transmitting coil and an internal receiving coil. The receiving coil, L1, is included and the transmitting parts of the system are excluded.

The implementation of the general concept of energy balance and the way the information is transmitted to the external energy transmitter can of course be implemented in numerous different ways. The schematic FIG. 13 and the above described method of evaluating and transmitting the information should only be regarded as examples of how to implement the control system.

Circuit Details

In FIG. 13 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. Please observe that the switch simply could mean any electronic circuit or component.

The embodiments described above identify a method and a system for controlling transmission of wireless energy to implanted energy consuming components of an electrically powered implantable medical device.

A method is thus provided for controlling transmission of wireless energy supplied to implanted energy consuming components of a device as described above. The wireless energy E is transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling transmission of wireless energy supplied to implanted energy consuming components of the device. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the device for directly or indirectly supplying received energy thereto. The system further comprises a determination device adapted to determine an energy balance between the energy received by the internal energy receiver and the energy used for the implantable energy consuming components of the device, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the device, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the device is consumed to operate the device, and/or stored in at least one energy storage device of the device.

Where electrical and/or physical parameters of the device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

Figure 14:
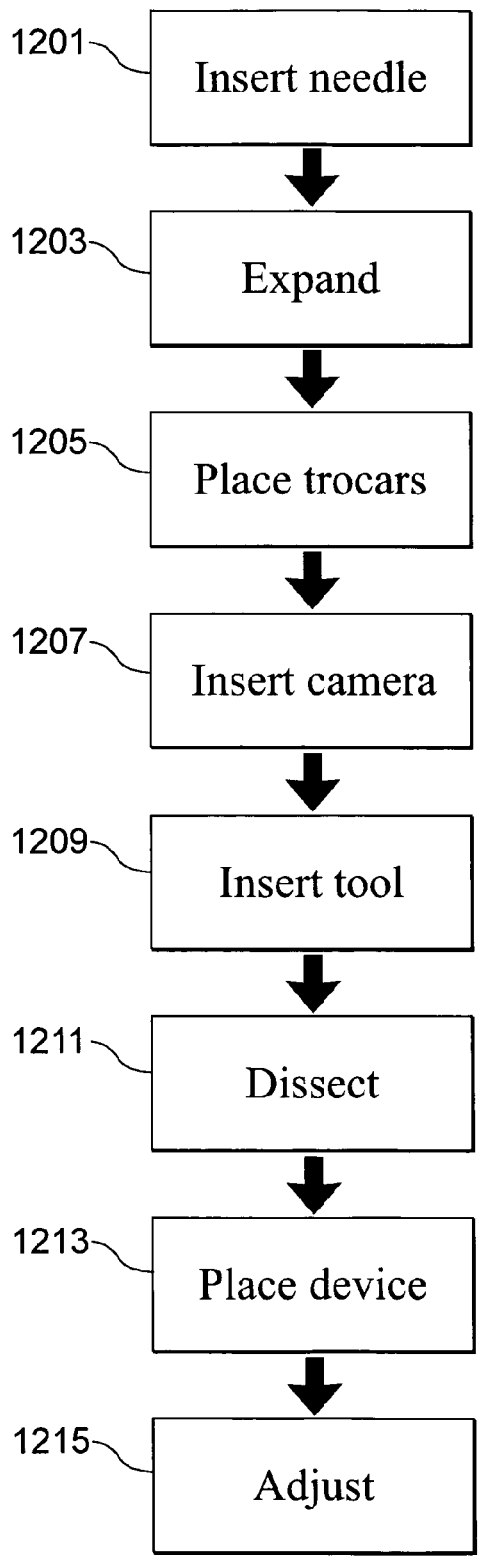
FIGS. 14-17 are flowcharts illustrating different surgical methods.

The device as described herein can be implanted in a patient using some suitable surgical procedure as depicted in FIG. 14. For example, the device can be implanted by inserting a needle or a tube like instrument into the patient's abdominal cavity, step 1201. Next in a step 1203 a part of the patient's body with gas using the needle or tube like instrument thereby expanding said abdominal cavity. Next in a step 1205 at least two laparoscopic trocars are placed in the cavity. Thereupon in a step 1207 a camera is inserted through one of the laparoscopic trocars into the cavity. Next in a step 1209 at least one dissecting tool is inserted through one of said at least two laparoscopic trocars. An area where the device is to be placed is then dissected in a step 1211. The device is then placed in the area in a step 1213, and the device is enabled in a step 1215.

Figure 15:
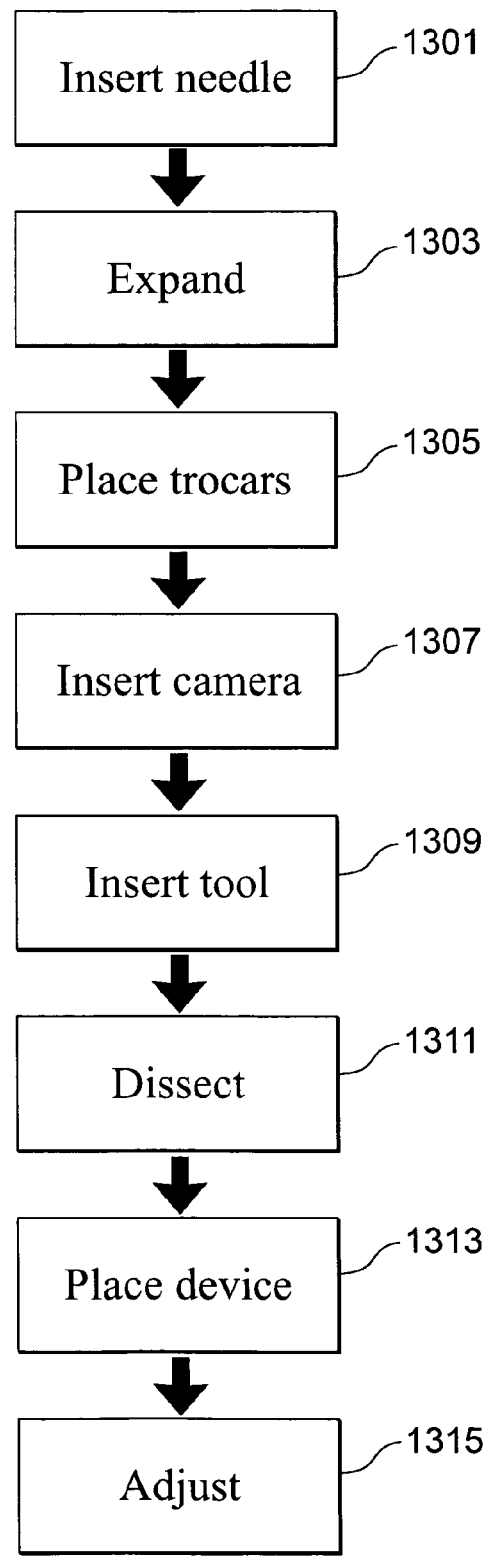

In accordance with one embodiment of the present invention the device can be implanted by a procedure depicted in FIG. 15. First in a step 1301 a needle or a tube like instrument is inserted into the patient's thoraxial cavity. Next, in a step 1303 a part of the patient's body with gas using the needle or tube like instrument to fill and thereby expanding the thoraxial cavity. Thereupon at least two laparoscopic trocars are placed in said cavity in a step 1305 Thereupon in a step 1307 a camera is inserted through one of the laparoscopic trocars into the cavity. Next in a step 1309 at least one dissecting tool is inserted through one of said at least two laparoscopic trocars. An area is then dissected in a step 1311. The device is then placed in the area in a step 1313, and the device is enabled in a step 1315.

Figure 16:
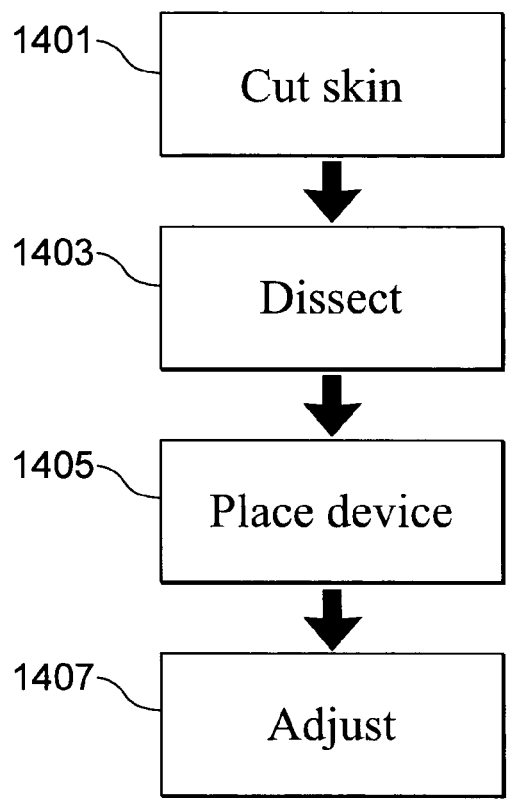

In accordance with one embodiment of the present invention the device can be implanted by a procedure depicted in FIG. 16. First in a step 1401, the skin in the abdominal or thoraxial wall of the mammal patient is cut. Next, in a step 1403 an area is dissected. Next, the device is then placed in the area in a step 1405, and the device is enabled in a step 1407.

Figure 17:
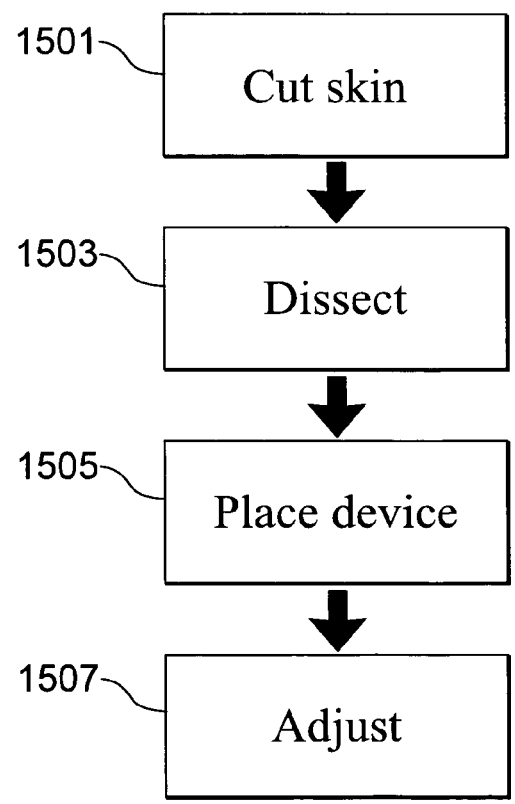

In accordance with one embodiment of the present invention the device can be implanted by a procedure depicted in FIG. 17. First in a step 1501, the skin of the mammal patient is cut. Next, in a step 1503 an area is dissected. Next, the device is then placed in the area in a step 1505, and the pressure that the device is enabled in a step 1507.

It should be noted that the description above illustrate some possible but non-limiting implementation options regarding how the various shown functional components and elements can be arranged and connected to each other.

However, the skilled person will readily appreciate that many variations and modifications can be made within the scope of the present invention.

Using the method and system as described herein will provide a more efficient transfer of energy from an external charger to an internal charger providing power to an implanted medical device.

Any embodiment or claim or part of embodiment or part of claim relating to a system comprising two coils, one implantable and one external coil, is also valid for the alternative with only an implantable coil adapted to receive energy from an external coil.

Please observe that any apparatus embodiment or claim is also valid for a method and may easily be converted to a method embodiment or method claim.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A system for supplying energy to a medical device apparatus implanted in a mammal patient, the medical device apparatus comprising: a receiver adapted to be implanted in a mammal patient's body, the receiver being adapted to receive energy from an external energizer adapted to transmit wireless energy to said receiver to thereby supply the medical implant apparatus with energy, wherein the receiver comprises:
    an internal first coil that, when implanted in the patient's body, receives wireless energy for supplying energy or control signals to the medical device apparatus, when implanted in the patient's body, and
    wherein the system comprises:
    an external second coil external to the patient's body that transmits the wireless energy to the first coil, when implanted in the patient's body, adapted to receive an alternating current that flows there-through, and wherein the wireless energy received by the first coil is an alternating magnetic field, which is created by the alternating current flowing in the second coil, the external second coil windings being made of a straight wire wound around a coil center axis, the center axis being adapted to be placed perpendicular to the skin of the patient, when transmitting the wireless energy,
    the internal first coil being wound from wire formed into a plurality of third coils connected to one another, with the plurality of third coils connected in parallel, and
    wherein the internal first coil comprises a plurality of large windings, each comprising first coil windings and second coil windings perpendicular to each other, the first coil windings each having a diameter that is smaller than the second coil winding's diameter.

2. The system of claim 1, wherein the large windings of the first coil are wound from wire formed into a plurality of third coils connected to one another,
    the internal first coil being wound from a helically shaped wire, the first coil windings comprising a helical winding that serves as the wire in the second larger diameter coil winding, and that is at adapted to at least one of:
    have a first diameter substantially smaller than the first coil's diameter,
    be wound in a compact manner like a tube,
    be used to wind the large windings of said first coil, and
    cause the first coil to be flexible.

3. The system of claim 2, wherein each of the third coils has a diameter that is substantially smaller then the first coil's diameter, and wherein, as the wire is wound to form the first coil, the plurality of third coils is caused to be positioned substantially perpendicular to a longitudinal axis of the first coil.

4. The system of claim 1, wherein the internal first coil is wound from a helically shaped wire that is flexible to prevent breakage of the wire.

5. The system of claim 1 further comprising a first control unit that, when implanted in the patient's body, is connected to the first coil so as to receive energy or control signals from the first coil or to provide information signals to the first coil for transmission to the second coil.

6. The system of claim 5 further comprising a second control unit that is located outside of the patient's body and connected to the second coil and is adapted to that generates energy or control signals for transmission to the first coil or receives information signals transmitted from the first coil.

7. The system of claim 6, wherein an alternating signal generated by the second control unit creates the alternating current that flows through the second coil, and wherein the alternating magnetic field induces an alternating voltage in the first coil.

8. The system of claim 7, wherein the alternating voltage induced in the first coil causes an electric charge to flow in the first coil to a load circuit connected to the internal first coil, so as to transfer energy from the external second coil through the internal first coil to the load circuit connected in the internal first coil.

9. The system of claim 8, wherein the load circuit is a power supply that, when implanted in the patient's body, supplies energy to the implanted medical device.

10. The system of claim 8, wherein the load circuit is the implanted medical device to which the first coil directly supplies energy, when implanted in the patient's body.

11. The system of claim 8, wherein the load circuit is the first control unit that, when implanted in the patient's body, supplies control signals to the implanted medical device.

12. The system of claim 11, wherein the control signals will relate to at least one of:
    bodily functions being monitored by the implanted medical device or bodily functions being controlled by the implanted medical device, and
    functional parameters of the medical device being monitored by the implanted medical device or functional parameters of the medical device being controlled by the implanted medical device.

13. The system of claim 8, wherein the load circuit is the first control unit that, when implanted in the patient's body, receives information signals from the implanted medical device.

14. The system of claim 13, wherein the information signals will relate to at least one of:
    bodily functions being monitored by the implanted medical device or bodily functions being controlled by the implanted medical device, and
    functional parameters of the medical device being monitored by the implanted medical device or functional parameters of the medical device being controlled by the implanted medical device.

15. The system of claim 6, wherein the second control unit is comprised of a generator for generating an alternating electromagnetic signal, a power amplifier, a modulator circuit, and a microprocessor for controlling the modulator circuit to thereby generate the control signals to be sent to the implanted medical device.

16. The system of claim 15, wherein the microprocessor controls the generator and the modulator circuit to modulate signals generated by the generator to thereby send control information to the implanted medical device via the power amplifier and the second coil, which is connected to the power amplifier.

17. The system of claim 5, wherein the first control unit is comprised of a generator for generating an alternating electromagnetic signal, a power amplifier, a modulator circuit, and a microprocessor for controlling the modulator circuit to thereby generate the information signals to be sent from the implanted medical device.

18. The system of claim 17, wherein the microprocessor controls the generator and the modulator circuit to modulate signals generated by the generator to thereby send to an external control unit bodily information from the implanted medical device via the power amplifier and the second coil, which is connected to the power amplifier.

19. The system of claim 17, wherein the first control unit is further comprised of a demodulator circuit that is connected to the first coil and that demodulates control signals received by the first coil so as to strip out control information sent from an external control unit, and
    the external control unit is further comprised of a demodulator circuit that is connected to the second coil and that demodulates information signals received by the second coil so as to strip out bodily information sent from the implanted medical device.

20. The system according to claim 1, wherein the internal first coil is adapted to be placed subcutaneously, the internal first coil having a large diameter and being adapted to be flexible enough for following the patient's movements, due to the helical structure of the coil wire, wherein the diameter of the first coil is large enough to allow a charging coil with a large diameter to be placed in the bed of the patient, allowing recharging when the patient is asleep.

21. The system according to claim 1, further comprising two or more implantable flexible first coils to allow a charging coil with a large diameter to be placed in the bed of the patient, thereby allowing recharging when the patient is asleep in different positions in the bed, charging different implantable first coils depending on the patient's position, wherein the two or more first coils are adapted to be placed at one or more of the following positions within the body abdominal wall outside, abdominal wall inside, pelvic area, the back, thoracic area, subcutaneously, thorax, abdomen, leg, arm, shoulder, and any other position in the body.

22. The system according to claim 1, wherein the internal first coil is adapted to be placed subcutaneously, having a large diameter and adapted to be flexible enough for following the patient's movements, due to the helical structure of the coil wire, the diameter of the first coil being at least one of:
    more than 0.5 cm, more than 1 cm, more than 2 cm, more than 5 cm, more than 10 cm,
    more than 15 cm, and more than 30 cm,
    or
    wherein an area of the first coil is at least one of:
    more than 0.5 $cm^2$, more than 2 $cm^2$, more than 10 $cm^2$, more than 100 $cm^2$, more than 300 $cm^2$,
    more than 500 $cm^2$, and more than 800 $cm^2$.

* * * * *